United States Patent
Savall et al.

(10) Patent No.: US 11,690,685 B2
(45) Date of Patent: *Jul. 4, 2023

(54) USER INTERFACE DEVICES FOR USE IN ROBOTIC SURGERY

(71) Applicant: Verb Surgical Inc., Santa Clara, CA (US)

(72) Inventors: Joan Savall, Palo Alto, CA (US); Allegra Anna Lenta Shum, San Francisco, CA (US); Jose Luis Cordoba, Malaga (ES); Yiqi Zeng, San Jose, CA (US)

(73) Assignee: Verb Surgical Inc., Santa Clara, CA (US)

( * ) Notice: Subject to any disclaimer, the term of this patent is extended or adjusted under 35 U.S.C. 154(b) by 31 days.

This patent is subject to a terminal disclaimer.

(21) Appl. No.: 17/385,830

(22) Filed: Jul. 26, 2021

(65) Prior Publication Data

US 2022/0015839 A1 Jan. 20, 2022

Related U.S. Application Data

(63) Continuation of application No. 16/888,335, filed on May 29, 2020, now Pat. No. 11,096,746, which is a
(Continued)

(51) Int. Cl.
*G05B 19/04* (2006.01)
*A61B 34/00* (2016.01)
(Continued)

(52) U.S. Cl.
CPC ............. *A61B 34/25* (2016.02); *A61B 34/00* (2016.02); *A61B 34/20* (2016.02); *A61B 34/30* (2016.02);
(Continued)

(58) Field of Classification Search
CPC ......... A61B 34/25; A61B 34/00; A61B 34/30; A61B 34/76; A61B 34/20; A61B 34/74;
(Continued)

(56) References Cited

U.S. PATENT DOCUMENTS

| | | | |
|---|---|---|---|
| 5,778,885 A | 7/1998 | Doyama et al. | |
| 6,697,044 B2 * | 2/2004 | Shahoian | A63F 13/06 345/156 |

(Continued)

FOREIGN PATENT DOCUMENTS

| | | |
|---|---|---|
| CN | 101566890 A | 10/2009 |
| CN | 102647955 A | 8/2012 |

(Continued)

OTHER PUBLICATIONS

Preliminary Office Action of the Brazilian Patent Office dated Feb. 15, 2022 for related Brazilian Patent Application No. BR112019010047-4.

(Continued)

*Primary Examiner* — Harry Y Oh
*Assistant Examiner* — Sohanatanju Tanju Khayer
(74) *Attorney, Agent, or Firm* — Aikin & Gallant, LLP

(57) ABSTRACT

A handheld user interface device for controlling a robotic system may include a member, a housing at least partially disposed around the member and configured to be held in the hand of a user, and a tracking sensor system disposed on the member and configured to detect at least one of position and orientation of at least a portion of the device. At least one of the detected position of the portion of the device and detected orientation of the portion of the device is correlatable to a control of the robotic system.

19 Claims, 20 Drawing Sheets

Related U.S. Application Data continuation of application No. 15/836,420, filed on Dec. 8, 2017, now Pat. No. 10,736,701.

(60) Provisional application No. 62/432,538, filed on Dec. 9, 2016.

(51) Int. Cl.

| | | |
|---|---|---|
| *A61B 34/20* | (2016.01) | |
| *A61B 34/30* | (2016.01) | |
| *B25J 13/02* | (2006.01) | |
| *A61B 17/00* | (2006.01) | |
| *A61B 90/00* | (2016.01) | |

(52) U.S. Cl.
CPC .............. *A61B 34/74* (2016.02); *A61B 34/76* (2016.02); *B25J 13/02* (2013.01); *A61B 17/00234* (2013.01); *A61B 90/361* (2016.02); *A61B 2017/00207* (2013.01); *A61B 2034/2048* (2016.02); *A61B 2034/2051* (2016.02); *A61B 2034/2055* (2016.02); *A61B 2034/301* (2016.02); *A61B 2034/302* (2016.02)

(58) Field of Classification Search
CPC .... A61B 2034/2051; A61B 2034/2048; A61B 2017/00207; A61B 2034/2055; A61B 2034/302; A61B 2034/301; A61B 17/00234; A61B 90/361; G06F 3/03547; G06F 3/0488; G06F 3/0338; G06F 3/033; G06F 3/0346; B25J 13/02
See application file for complete search history.

(56) References Cited

U.S. PATENT DOCUMENTS

| | | | | |
|---|---|---|---|---|
| 7,643,862 | B2* | 1/2010 | Schoenefeld | A61B 34/20 600/407 |
| 2009/0267897 | A1 | 10/2009 | Ootsuka | |
| 2012/0011932 | A1 | 1/2012 | Nakagawa et al. | |
| 2012/0303839 | A1 | 11/2012 | Jackson et al. | |
| 2013/0321262 | A1 | 12/2013 | Schecter | |
| 2015/0153842 | A1 | 6/2015 | Obermeyer et al. | |
| 2018/0168759 | A1* | 6/2018 | Kilroy | A61B 34/74 |

FOREIGN PATENT DOCUMENTS

| | | | | |
|---|---|---|---|---|
| CN | 105934215 | A | 9/2016 | |
| EP | 2869780 | B1 * | 11/2018 | ......... A61B 17/1703 |
| EP | 2869780 | B1 | 11/2018 | |
| JP | 06-095800 | A | 4/1994 | |
| JP | 11-194882 | A | 7/1999 | |
| JP | 2012-022548 | A | 2/2012 | |
| JP | 2012-099047 | A | 5/2012 | |
| JP | 2012099047 | A * | 5/2012 | |
| JP | 2016-149306 | A | 8/2016 | |
| WO | 2016/116722 | A1 | 7/2016 | |
| WO | 2016/140924 | A1 | 9/2016 | |
| WO | 2016/171757 | A1 | 10/2016 | |

OTHER PUBLICATIONS

Corrected Notice of Allowability of the U.S. Patent Office dated Jul. 16, 2020 for related U.S. Appl. No. 15/836,420.
Corrected Notice of Allowability of the U.S. Patent Office dated May 28, 2020 for related U.S. Appl. No. 15/836,420.
Examination Repod No. 1 of the Australian Patent Office dated Jun. 25, 2019 for related Australian Patent Application No. 2017371074.
Examination Report No. 1 of the Australian Patent Office dated May 14, 2020 for related Australian Patent Application No. 2019275547.
Examination Report No. 1 of the Australian Patent Office dated May 22, 2021 for related Australian Patent Application No. 2020250296.
Examiner's Report of the Canadian Patent Office dated Apr. 29, 2020 for related Canadian Patent Application No. 3042739.
Extended European Search Report of the EP Patent Office dated May 25, 2020 for related EP Patent Application No. 17877599.5.
International Search Report and Written Opinion of the PCT Patent Office dated Feb. 12, 2018 for related PCT Patent Application No. PCT/US2017/065372.
Non-Final Office Action of the U.S. Patent Office dated Dec. 11, 2020 for related U.S. Appl. No. 16/888,335.
Non-Final Office Action of the U.S. Patent Office dated Dec. 17, 2019 for related U.S. Appl. No. 15/836,420.
Notice of Acceptance of the Australian Patent Office dated Aug. 28, 2019 for related Australian Patent Application No. 2017371074.
Notice of Acceptance of the Australian Patent Office dated Aug. 31, 2020 for related Australian Patent Application No. 2019275547.
Notice of Allowance of the Korean Patent Office dated Jun. 17, 2021 for related Korean Patent Application No. 10-2019-7016406.
Notice of Allowance of the U.S. Patent Office dated Apr. 12, 2021 for related U.S. Appl. No. 16/888,335.
Notice of Allowance of the U.S. Patent Office dated Apr. 21, 2021 for related U.S. Appl. No. 16/888,335.
Notice of Allowance of the U.S. Patent Office dated Jul. 21, 2021 for related U.S. Appl. No. 16/888,335.
Notice of Allowance of the U.S. Patent Office dated Mar. 31, 2020 for related U.S. Appl. No. 15/836,420.
Notice of Allowance of the U.S. Patent Office dated May 27, 2021 for related U.S. Appl. No. 16/888,335.
Notice of Final Rejection of the Korean Intellectual Property Office dated Apr. 21, 2021 for related Korean Patent Application No. 10-2019-7016406.
Notice of Reasons for Refusal of the Japanese Patent Office dated Apr. 30, 2021 for related Japanese Patent Application No. 2019-528634.
Notification of Reason for Refusal of the Korean Patent Office dated Oct. 30, 2020 for related Korean Patent Application No. 10-2019-7016406.
Notification to Grant Patent of the Chinese Patent Office dated May 18, 2021 for related Chinese Patent Application No. 201780004134.2.
Office Action of the Chinese Patent Office dated Jul. 21, 2020 for related Chinese Patent Application No. 201780004134.2.
Office Action of the Japanese Patent Office dated May 20, 2020 for related Japanese Patent Application No. 2019-528634.
Office Action of the Japanese Patent Office dated Sep. 7, 2020 for related Japanese Patent Application No. 2019-528634.
Second Office Action of the Chinese Patent Office dated Jan. 28, 2021 for related Chinese Patent Application No. 201780004134.2.
Decision to Grant a Patent of the Japanese Patent Office dated Oct. 6, 2021 for related Japanese Patent Application No. 2019-528634.
International Preliminary Report on Patentability of the PCT Patent Office dated Jun. 20, 2019 for related PCT Patent Application No. PCT/US2017/065372.
Notice of acceptance for patent application of the Australian Patent Office dated Jul. 30, 2021 for related Australian Patent Application No. 2020250296.
Office Action of the EP Patent Office dated Jun. 12, 2020 for related EP Patent Application No. 17877599.5.
Wei et al., "An Overview Of Micro-force Sensing Techniques", Sensors and Actuators A: Physical, vol. 234, Oct. 1, 2015, p. 359-374. (Manuscript).

* cited by examiner

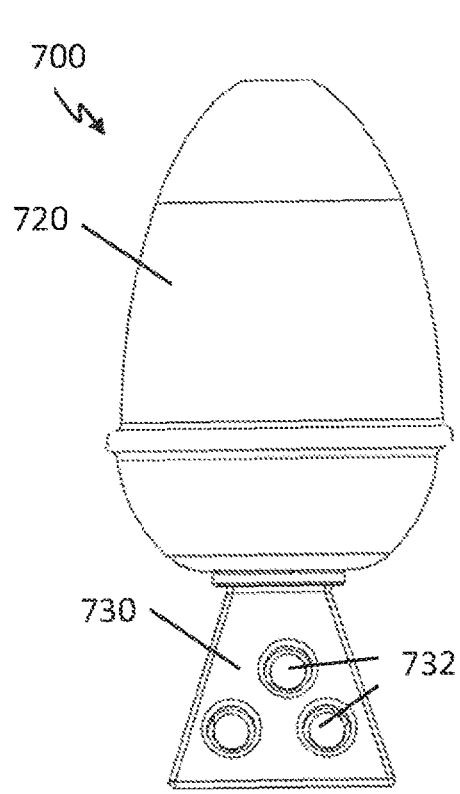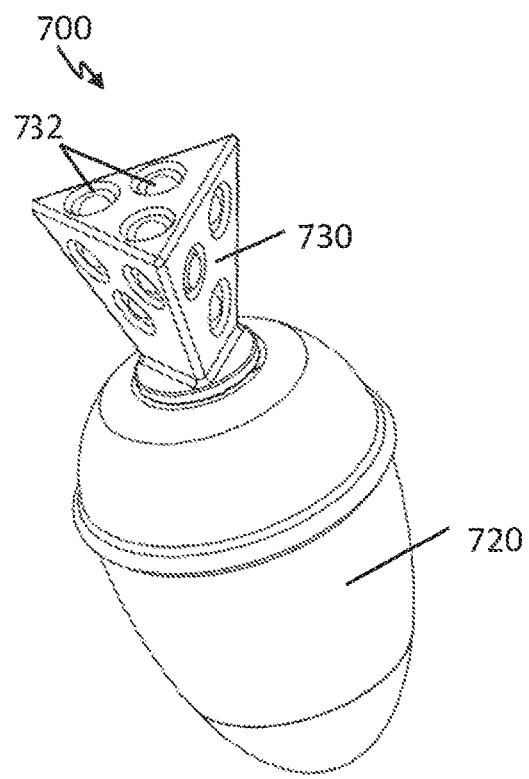
FIG. 7A     FIG. 7B
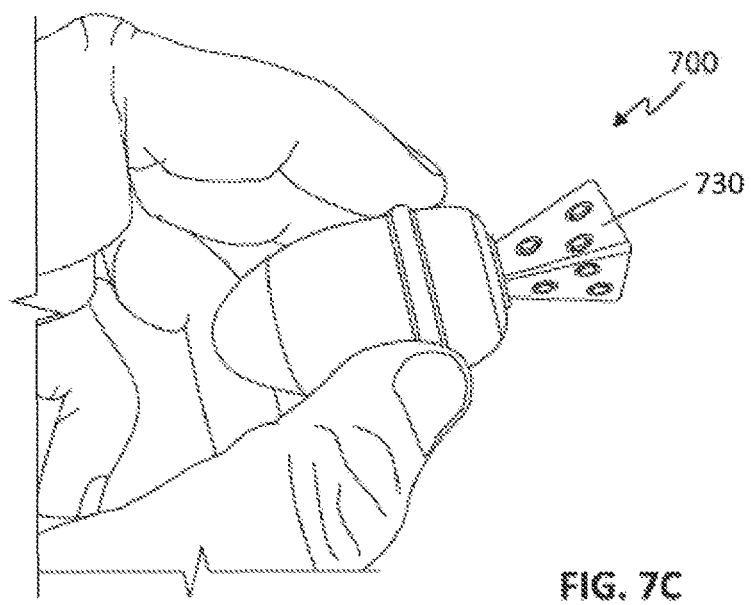
FIG. 7C

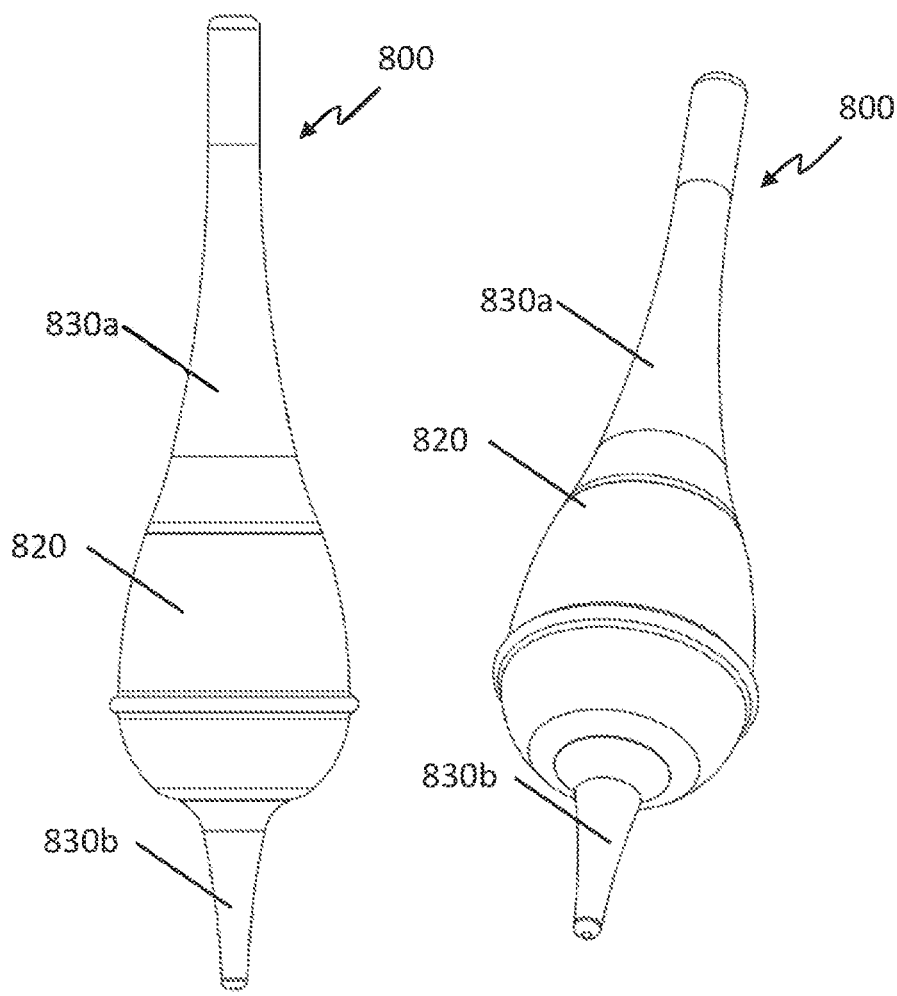

USER INTERFACE DEVICES FOR USE IN ROBOTIC SURGERY

CROSS-REFERENCE TO RELATED APPLICATIONS

This application is a continuation of U.S. patent application Ser. No. 16/888,335, filed on May 29, 2020, which is a continuation of U.S. patent application Ser. No. 15/836,420, filed on Dec. 8, 2017, now issued as U.S. Pat. No. 10,736,701, which claims priority to U.S. Patent Application Ser. No. 62/432,538, filed on Dec. 9, 2016. The entire contents of each of which are hereby incorporated by reference as if fully set forth herein.

TECHNICAL FIELD

This disclosure relates generally to robotic-assisted systems and, more particularly, to user interface devices for controlling robotic-assisted surgical systems.

BACKGROUND

Minimally-invasive surgery (MIS), such as laparoscopic surgery, involves techniques intended to reduce tissue damage during a surgical procedure. For instance, laparoscopic procedures typically involve creating a number of small incisions in the patient (e.g., in the abdomen), and introducing one or more tools and at least one camera through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery.

MIS may be performed with non-robotic or robotic systems. Conventional robotic systems, which may include robotic arms for manipulating tools based on commands from an operator, may provide many benefits of MIS while reducing demands on the surgeon. Control of such robotic systems may require control inputs from a user (e.g., surgeon or other operator) via one or more user interface devices that translate manipulations or commands from the user into control of the robotic system. However, conventional user interface devices for robotic surgical systems may have drawbacks. For example, conventional user interface devices may not be ergonomically designed, which may lead to user discomfort or fatigue and possible negative effects on the surgery. Thus, it is desirable to have new and improved user interface devices, particularly for use in robotic surgery.

SUMMARY

Generally, in one variation, a handheld user interface device for controlling a robotic system may include a member, a housing at least partially disposed around the member and configured to be held in the hand of a user, at least one capacitive sensor configured to detect interaction between the hand of the user and the housing, and a tracking sensor system configured to detect at least one of position and orientation of at least a portion of the device. At least one of the detected interaction, detected position of the portion of the device, and detected orientation of the portion of the device may be correlatable to a control of the robotic system.

The detected position or detected orientation of the portion of the device may, for example, be correlatable to control of a robotic arm or an end effector. The capacitive sensor may, for example, detect interaction such as the hand-based squeezing of the housing by measuring changes in proximity between the hand of the user and the capacitive sensor. As another example, the capacitive sensor may be configured to detect the hand of the user squeezing the housing by measuring proximity between a first conductive surface on the housing and a second conductive surface on the housing. As another example, the same or a second capacitive sensor may include a plurality of discrete sensor regions configured to detect user-initiated gestures (e.g., swiping) performed with the user interface device (e.g., correlatable to control of a graphical user interface of the robotic system, or other control). As another example, the capacitive sensor may detect interaction such as disengagement between the housing and the hand of the user (e.g., dropping the user interface device or mounting the user interface device in a device holder) that triggers a suspension in control of the robotic system.

Generally, in another variation, a handheld user interface device for controlling a robotic system may include a member, a flexible housing at least partially disposed around the member and configured to be held in the hand of a user, at least one proximity sensor configured to detect deformation of the housing, and a tracking sensor system configured to detect at least one of position and orientation of at least a portion of the device. At least one of the detected deformation of the housing, detected position of the portion of the device, and detected orientation of the portion of the device may be correlatable to a control of the robotic system.

The detected position or detected orientation of the portion of the device may, for example, be correlatable to control of a robotic arm or an end effector. The proximity sensor may, for example, be configured to detect deformation of the housing that is correlatable to an opening or closing of an end effector (e.g., jaws) of the robotic system. The proximity sensor may be configured to detect such deformation of the housing by being configured to measure a change in distance between the member and a flexing member configured to deflect upon deformation of the housing. In some variations, the proximity sensor may be an optical sensor, though other kinds of proximity sensors may be used.

Generally, in another variation, a handheld user interface device for controlling a robotic system may include a member having a first end and a second end (e.g., a proximal end and a distal end), wherein at least one of the first and second ends comprises an engagement feature configured to couple to a detachable adapter, a housing at least partially disposed around the member and configured to be held in the hand of a user, and a tracking sensor system configured to detect at least one of position and orientation of at least a portion of the device. At least one of the detected position and detected orientation of the portion of the device may be correlatable to a control of the robotic system.

The detected position or detected orientation of the portion of the device may, for example, be correlatable to control of a robotic arm or an end effector. The member may be removably coupled, for example, from one or more detachable adapters such as an optical tracker adapter with optical tracking markers to provide information regarding position and/or orientation of the optical tracker adapter, a stylus, a disc adapter or joystick, a button, pinchers, etc. Such adapters may, for example, provide application-specific or other suitable functional customizations for operating different kinds of end effectors of the robotic system, etc.

Generally, in another variation, a handheld user interface device for controlling a robotic system may include a member, a housing at least partially disposed around the member and configured to be held in the hand of a user, and a tracking sensor system disposed on the member and configured to detect at least one of position and orientation of at least a portion of the device. At least one of the detected position and detected orientation of the portion of the device may be correlatable to a control of the robotic system. The detected position or detected orientation of the portion of the device may, for example, be correlatable to control of a robotic arm or an end effector. In some variations, at least a portion of the tracking system may be removable from at least one of the member and the housing to enable disposal of at least one of the member and housing. Such disposal may, for example, reduce the need for maintaining sterility of all the components of the user interface device for separate uses of the user interface device. In some variations, the housing may be selected from a set of housings having different sizes suitable for different kinds (e.g., shapes, sizes, etc.) of user hands.

BRIEF DESCRIPTION OF THE DRAWINGS

FIGS. 7A and 7B are perspective views of one variation of a handheld user interface device with an optical tracking adapter. FIG. 7C is an exemplary illustration of the handheld user interface device depicted in FIGS. 7A and 7B, held in a hand of a user.

FIGS. 8D and 8DD are side and perspective views of another variation of a handheld user interface device with a stylus adapter.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

Figure 1A:
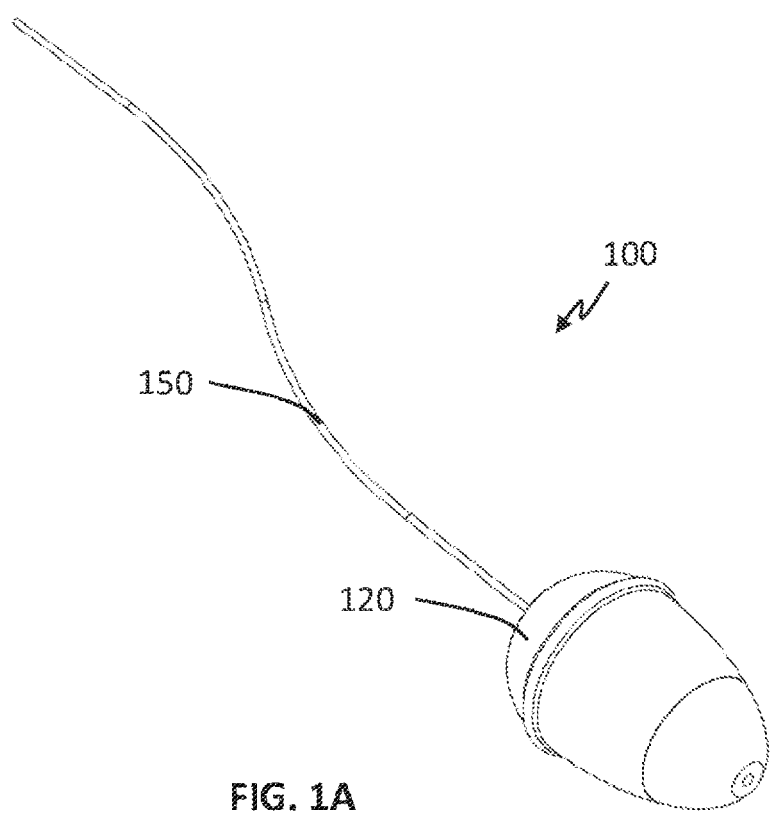
FIG. 1A is an illustrative schematic of a variation of a wired handheld user interface device.

As shown generally in FIGS. 1A-IC, a handheld user interface device 100 for controlling a robotic system may include a member 110, a housing 120 at least partially disposed around the member and configured to be held in the hand of a user, and a tracking sensor system 140 configured to detect at least position and/or orientation of at least a portion of the device. The detected position and/or orientation of the device may be correlatable to a control of the robotic system. For example, the user interface device 100 may control at least a portion of a robotic arm, an end effector or tool (e.g., graspers or jaws) coupled to a distal end of the robotic arm, a graphical user interface, or other suitable aspect or feature of a robotic system. Additional exemplary correlations are described in further detail below.

The user interface device may include a clutch mechanism for enabling toggling between different control modes (e.g., switching between controlling a robotic arm and controlling an end effector, between controlling a robotic arm or end effector and a graphical user interface, etc.). One or more of the various user inputs described in further detail below may function as a clutch that, when engaged, changes the correlation of the position and/or orientation of the user interface device (or squeezing, gesturing, or other suitable input) to a different control of the robotic system. For example, touching a gesture touch region of the device, squeezing the housing, pushing or tilting a disc adapter, etc. may function as a clutch.

Generally, a user interface for controlling a robotic surgical system may include at least one handheld user interface device 100, or may include at least two handheld user interface devices 100 (e.g., a first user interface device to be held by a left hand of the user, and a second user interface device to be held by a right hand of the user), three handheld user interface devices 100, or any suitable number. Each user interface device 100 may be configured to control a different aspect or feature of the robotic system. For example, a user interface device held in the left hand of the user may be configured to control an end effector represented on a left side of a camera view provided to the user, while a user interface device held in the right hand of the user may be configured to control an end effector represented on a right side of the camera view. The control inputs to the user interface device 100 may, for example, be provided by the user as user commands during the course of providing a diagnostic, surgical, laparoscopic or minimally invasive surgical procedure, or other robotic procedure.

In some variations, the handheld user interface device 100 may be a groundless user interface device configured to be held in the hand and manipulated in free space. For example, the user interface device 100 may be configured to be held between the fingers of a user, and moved about freely (e.g., translated, rotated, tilted, etc.) by the user as the user moves his or her arms, hands, and/or fingers. Additionally or alternatively, the handheld user interface device 100 may be a body-grounded user interface device, in that the user interface device 100 may be coupled to a portion of the user (e.g., to fingers, hand, and/or arms of a user) directly or via any suitable mechanism such as a glove, hand strap, sleeve, etc. Such a body-grounded user interface device may still enable the user to manipulate the user interface device in free space. Accordingly, in variations in which the user interface device 100 is groundless or body-grounded (as opposed to permanently mounted or grounded to a fixed console or the like), the user interface device 100 may be ergonomic and provide dexterous control, such as by enabling the user to control the user interface device with natural body movements unencumbered by the fixed nature of a grounded system.

Figure 1B:
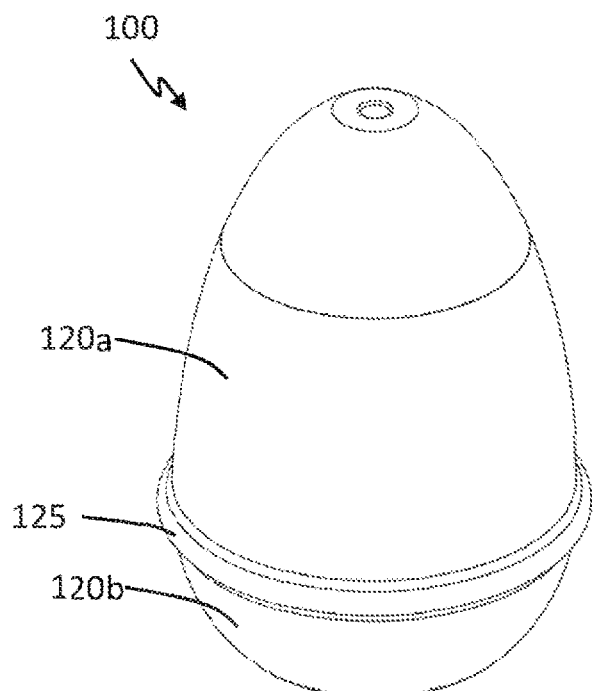
FIG. 1B is an illustrative schematic of a variation of a wireless handheld user interface device.
Figure 2A:
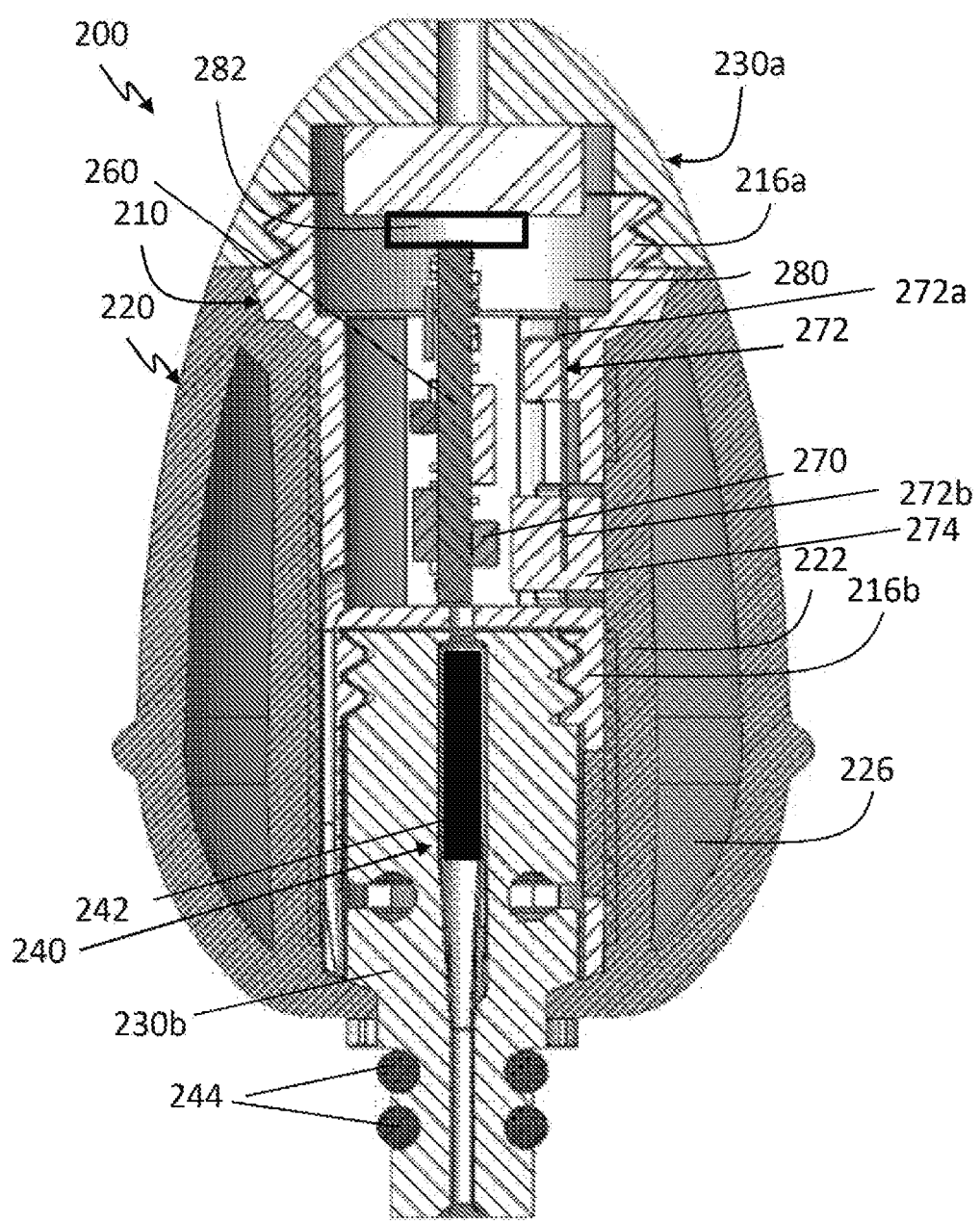
FIG. 2A is a longitudinal cross-sectional view of a variation of a handheld user interface device with an optical sensor.
Figure 2B:
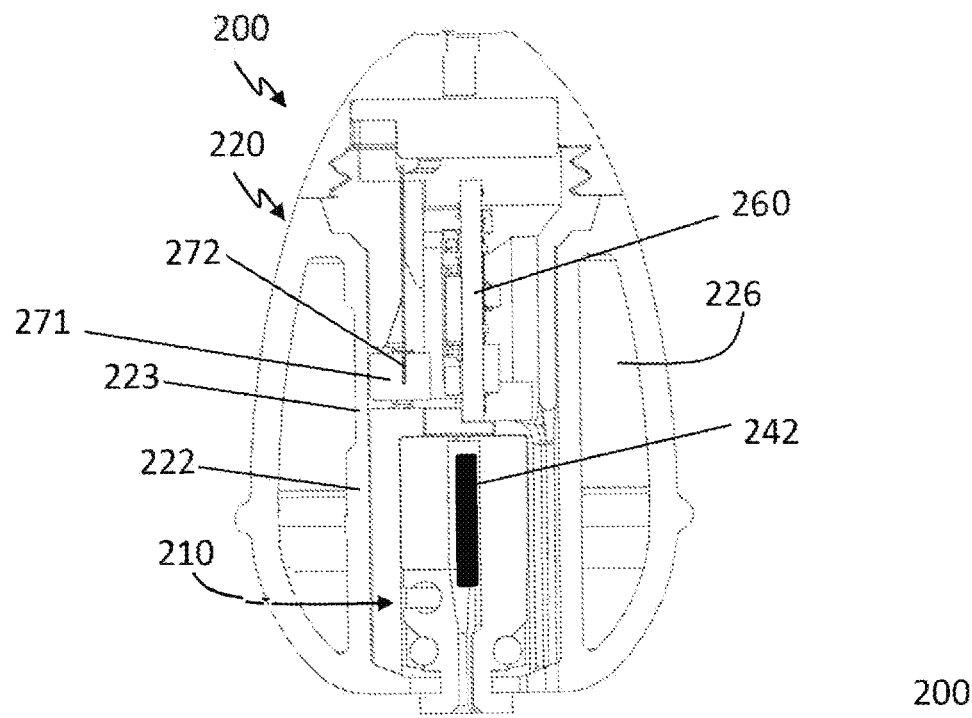
FIG. 2B is a longitudinal cross-sectional view of a variation of a handheld user interface device with an optical sensor.
Figure 2C:
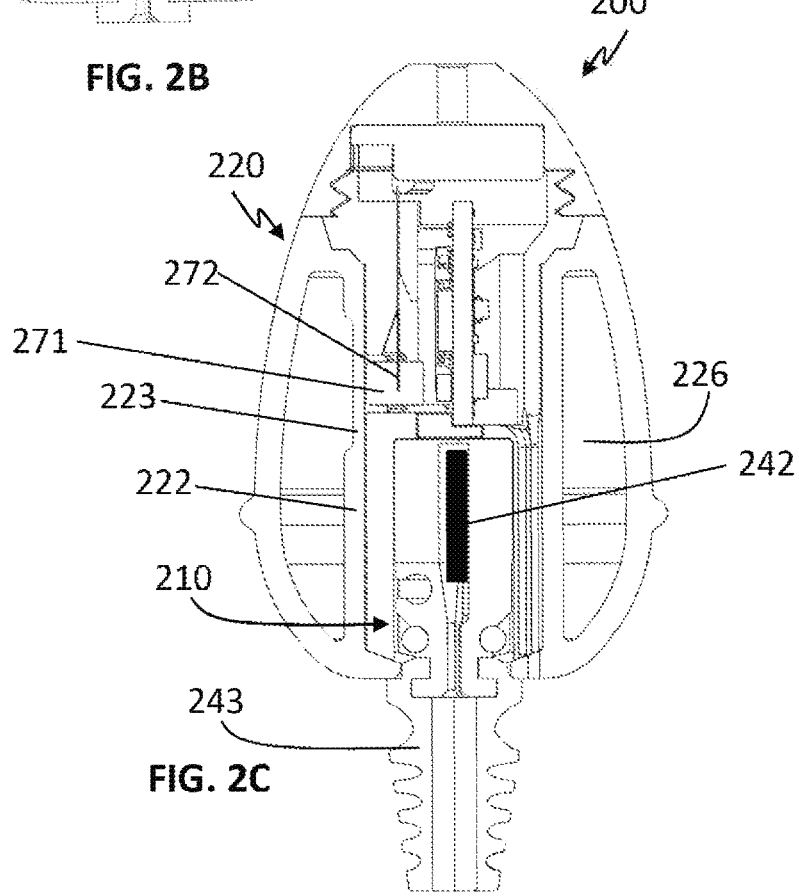
FIG. 2C is a longitudinal cross-sectional view of a variation of a handheld user interface device with an optical sensor and strain relief for a wired tracking sensor system.

The handheld user interface device 100 may include wired connections (e.g., with a wire 150 coupling the user interface device 100 to an external control system) as shown in FIG. 1A. The wires may, for example, provide power to the user interface device 100, carrying sensor signals (e.g., from the tracking sensor assembly and/or other sensors such as a capacitive sensor, optical sensor, etc. described below). In one example, as shown in FIG. 2A, a wired connection (e.g., to the tracking sensor system) may be secured to the housing or otherwise supported with O-rings 244, epoxy, etc. that help prevents the wired connection from disengaging from the rest of the handheld user interface 200. As another example, as shown in FIG. 2C, a wired connection (e.g., to the tracking sensor system) may additionally or alternatively be supported by a strain relief 243 that flexes and helps reduce strain experienced by the wire as the user interface device is manipulated. As another example, as shown in FIG. 2B, the wired connection may omit a strain relief. Alternatively, the user interface device may be wireless as shown in FIG. 1B (and FIGS. 7A and 7B) and communicate commands and other signals via wireless communication such as radiofrequency signals (e.g., WiFi or short-range such as 400-500 mm range, etc.) or other suitable wireless communication protocol such as Bluetooth. Other wireless connections may be facilitated with sensors such as optical reader sensors and/or cameras configured to detect optical markers on the user interface device 100 as described further below, infrared sensors, ultrasound sensors, or other suitable sensors.

Housing

The housing 120 may be configured to be held in the hand of a user, and generally may provide a gripping volume with which the user may interact. For example, at least a portion of the housing 120 may be configured to be grasped, pinched, rolled, squeezed, shaken, or otherwise held or manipulated between fingers of the user's hand.

As shown in FIG. 1B, in some variations, the housing may generally include at least a first portion 120a and a second portion 120b. The housing may be configured to be held in the hand of a user such that the first portion 120a is directed proximally (i.e., the first portion 120a is a proximal section of the housing) and the second portion 120b is directed distally (i.e., the second portion 120b is a distal section of the housing), though alternatively in different variations and/or applications, the first and second portions 120a and 120b may be directed distally and proximally respectively, or in other suitable directions.

Figure 1C:
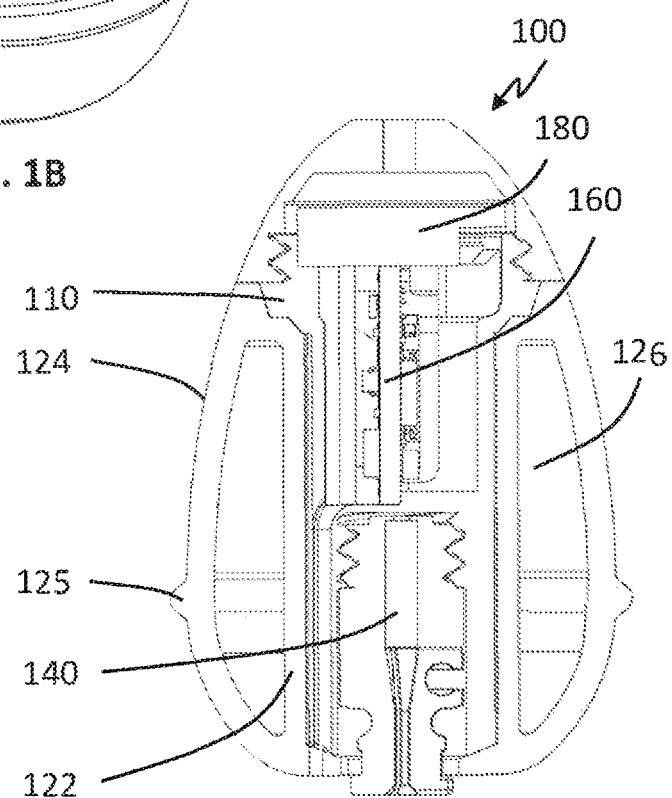
FIG. 1C is a longitudinal cross-sectional view of a variation of a handheld user interface device.

As shown in FIGS. 1A-1C, the housing 120 may be generally rounded, with the first and second portions 120a and 120b being contoured or tapered. For example, the housing 120 may be generally ovoid or egg-shaped (e.g., the first portion 120a may be longer and have a more gradual contour or taper than the second portion 120b). The housing 120 may have a radially-symmetrical profile about a longitudinal axis. The housing may generally have a length (measured along the longitudinal axis) and a width (measured transverse to the longitudinal axis), where the length is longer than the width. The first and second portions 120a and 120b may have different radii of curvature.

In some variations, the housing 120 may define at least one circumferential or partial circumferential lip or raised ring 125. The lip 125 may provide a tactile reference point for the location of the user's grip on the surface of the user interface device 100, provide a frictional textured surface for improved grip, etc. For example, the lip 125 may be disposed between the first portion 120a and second portion 120b of the housing, though alternatively, the lip 125 may be disposed on any suitable portion of the housing. In some variations, the housing 120 may additionally or alternatively include other textural enhancements (e.g., multiple lips or raised surfaces forming a pattern, one or more recessed grooves, etc.).

Figures 10A, 10B, 10C:
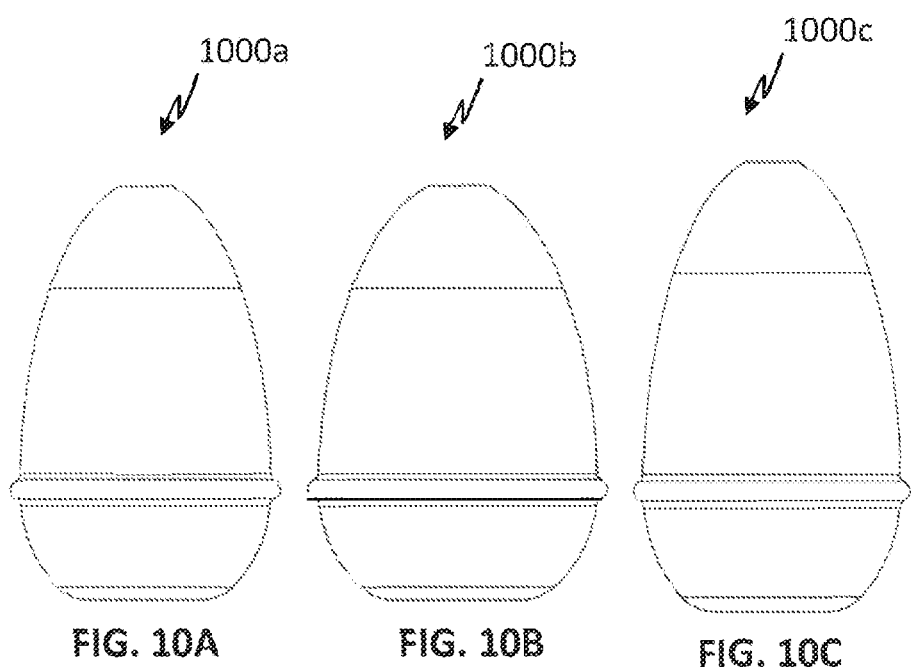
FIGS. 10A-10C are illustrative schematics of exemplary user interface devices of different sizes and shapes.

The housing 120 may be customized or designed for different hand sizes and/or shapes. For example, the housing 120 may be selected from a plurality of housing sizes suitable for a range of hand sizes and/or shapes. As another example, the housing 120 may be customized for a specific user's hand (e.g., based at least partially on a mold). The housing 120 may vary in girth, length, and/or in any suitable dimension or other feature. For example, relative to one exemplary variation of a user interface device 1000a shown in FIG. 10A, a user interface device 1000b as shown in FIG. 10B may be wider in girth, and a user interface device 1000c as shown in FIG. 10C may be longer. Furthermore, different housing portions (e.g., first and second portions 120a and 120b) may vary individually or together. For example, a first variation and a second variation of the housing 120 may be similar in that they both have a first portion 120a with the same size and shape, but differ in that the first variation has a narrower second portion 120b and the second variation has a wider second portion 120b. As another example, a third variation of the housing 120 may include a shorter first portion 120a and a narrower second portion 120b relative to a fourth variation of the housing 120 that includes a longer first portion 120a and a wider second portion 120b. Furthermore, the textural pattern on the exterior surface of the housing may vary, such as in height and/or thickness. Shape of the textural pattern, other special formations of the textural pattern (e.g., an identification code), or the like may, in some examples, correspond to a particular SKU or part number indicating the size and/or shape of the housing.

As shown in FIG. 1C, the housing 120 may include an inner wall 122 and an outer wall 124. The inner wall 122 may define a lumen configured to receive the member 110. The inner wall 122 and the outer wall 124 may cooperate to define a volume 126 between the inner and outer walls, such that the housing 120 includes a bladder.

The housing 120 may be compliant and deformable, where deformation of the housing is correlatable to a control of the robotic system (e.g., squeezing the housing may be correlated to a pinching control of an end effector with jaws). For example, the volume 126 of the housing 120 may be filled with a fluid. For example, the volume 126 or bladder may be filled with a pressurized gas (e.g., air), fluid (e.g., silicone oil, saline, water, etc.), or a semi-fluid substance. Additionally or alternatively, the housing 120 may be made at least partially of a flexible material such as silicone, latex, or other suitable polymer or alloy. The housing material may be a suitable medical grade material. Furthermore, at least a portion of the housing material may be sterilizable (e.g., by autoclave, wipe-down, etc.) and/or may be removable from the rest of the device in order to facilitate disposal.

Figure 12:
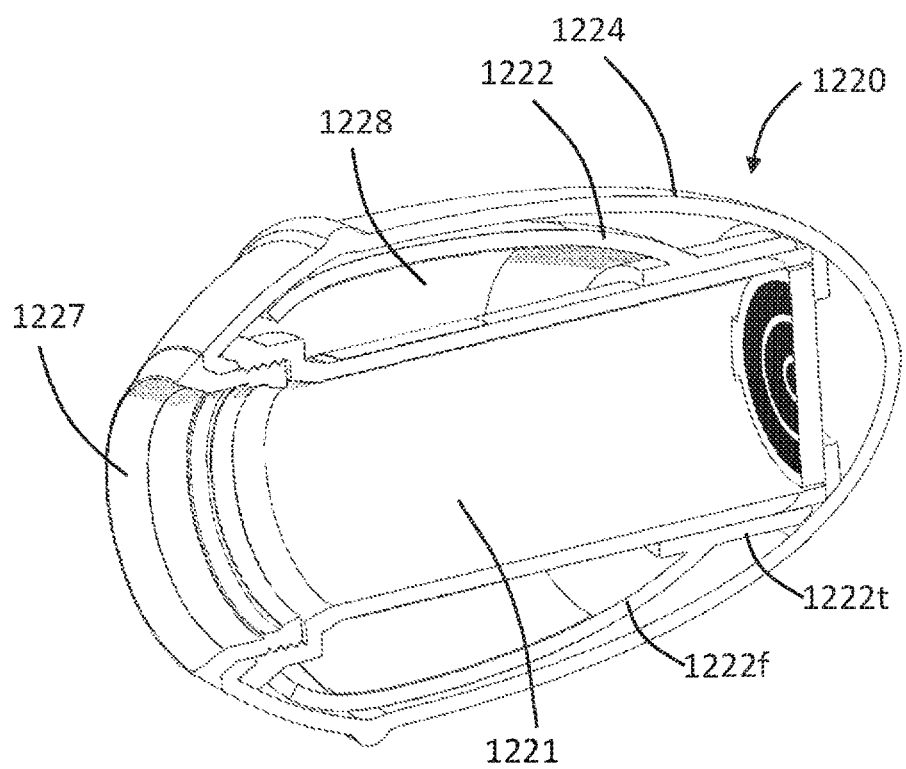
FIG. 12 is a longitudinal cross-sectional view of another variation of a handheld user interface device with separate inner and outer housing layers.

Although in some variations, as shown in FIG. 1C, the inner wall 122 and outer wall 124 may be part of the same integrally formed housing 120, in other variations the housing may include multiple, separately formed portions forming at least part of the inner wall 122 and at least part of the outer wall 124. For example, as shown in FIG. 12, one variation of a housing 1220 may include an inner housing layer 1222 forming an inner wall, and an outer housing layer 1224 forming an outer wall. The housing may further include a liner 1221 disposed within a lumen of the inner housing layer 1222 and configured to receive the member (not shown). The liner 1221 may include a rigid or semi-rigid member (e.g., made of nylon, polycarbonate, or any suitable material) for providing structure support to the housing 1220. For example, the inner housing layer 1222 may include a tubular portion 1222*t* that receives and couples to the liner 1221 (e.g., via friction fit), and a flared portion 1222*f* coupled to the tubular portion 1222*t*. The flared portion 1222*f* may widen or flare radially outward such that the inner housing layer 1222 and the liner 1221 cooperate to define a volume between the inner housing layer 1222 and the liner 1221. The volume may function in a similar manner as volume 126 described above with reference to FIG. 1C. For example, the inner and outer housing layers may be made of a flexible, pliable material (e.g., silicone) to enable deformation of the inner housing layer 1222 (e.g., as measured with one or more capacitive squeeze sensors as described below). Deformation of the inner housing layer 1222, and the resulting deformation of the volume, may be correlatable to a control of the robotic system. Although only one inner housing layer 1222 and one outer housing layer 1224 are shown in FIG. 12, it should be understood that in other variations, any suitable number of layers (e.g., three, four, etc.) may be included in the housing 1220. Furthermore, any layer may include one or more parts joined together (e.g., the inner housing layer 1222 may include a tubular portion 1222*t* that is separately formed from, and later coupled to, the flared portion 1222*f*).

Figure 13A:
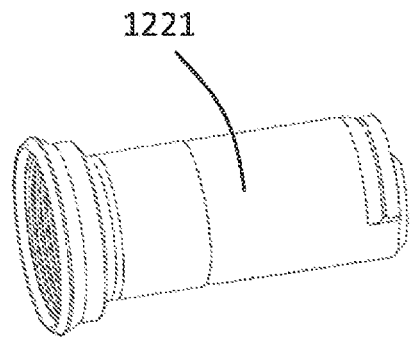
FIGS. 13A-13D illustrate steps of a method of assembly of the handheld user interface device depicted in FIG. 12.

An exemplary method of partial assembly of the housing 1220 and liner 1221 shown in FIG. 12 is illustrated by the sequence of FIGS. 13A-13D. FIG. 13A depicts a liner 1221.

Figure 13B:
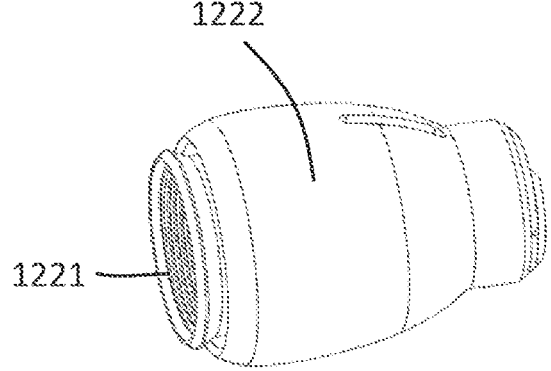
Figure 13C:
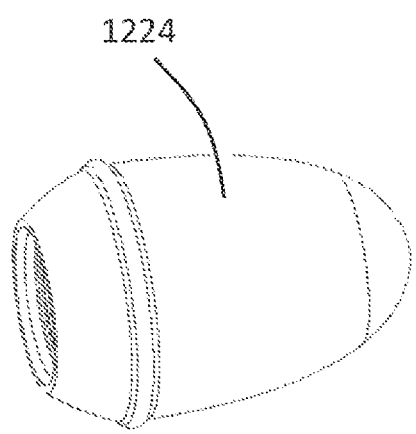
Figure 13D:
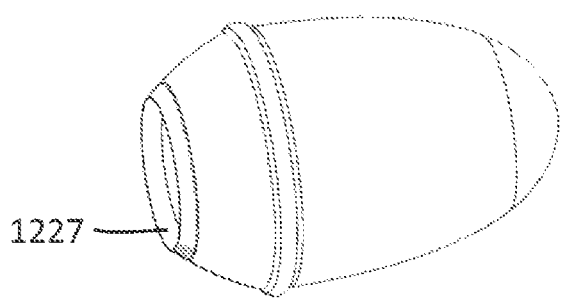

As shown in FIG. 13B, the inner housing layer 1222 may couple to the liner 1221 (e.g., via friction fit) by passing over the liner 1221 and receiving the liner 1221 within the lumen of the tubular portion 1222*t* shown in FIG. 12. For example, the inner housing layer 1222 may be longitudinally passed or slipped over the liner 1221. As another example, the inner housing layer 1222 may include a longitudinal slit or other opening that enables the inner housing layer 1222 to open laterally and enclose at least a part of the liner 1221. As shown in FIG. 13C, the outer housing layer 1224 may enclose the inner housing layer 1222 and liner 1221 subassembly. Finally, as shown in FIG. 13D, a collar 1227 may secure the outer housing layer 1224 to the inner housing layer 1222 and liner 1221 subassembly (e.g., help prevent the outer housing layer 1224 from slipping off). The collar 1227 may, for example, as shown in cross-sectional detail in FIG. 12, threadingly engage the liner 1221 and compress the end of the outer housing layer 1224 between the collar 1227 and the liner 1221. Alternatively, the collar 1227 may engage and secure the outer housing layer 1224 to the inner housing layer 1222 and/or the liner 1221 via a snap fit or other suitable manner.

Member

As shown in FIG. 1C, the user interface device 100 may include at least one member 110. The member may generally have a circular cross-sectional shape. The member 110 may be disposed along a central, longitudinal axis within the housing 120 (e.g., along an axis of rotation, in variations in which the housing 120 is radially symmetrical) such that the tracking sensor system disposed on or within the member 110 can more easily and accurately distinguish between orientation changes of the device due to rotation (e.g., roll, pitch, or yaw) and absolute position changes of the device due to translation or displacement. Alternatively, in other variations, the member 110 may be included in or disposed in any suitable portion of the housing 120, with a suitable compensation for any offset of the member 110 from an axis of rotation. The member 110 may extend substantially along the length of the housing 120, or any suitable portion of the length of the housing 120.

In some variations, the member 110 may include a lumen or other internal volume configured to receive various electronics and/or other components. For example, the internal volume may include at least one printed circuit board 160 (PCB) having one or more sensors described in further detail below. As another example, as shown in FIG. 2A, a battery 282 may be disposed within the internal volume for powering the PCB and other electrical components in the user interface device 110. Although the battery 282 is depicted adjacent motor 280, the battery may alternatively be located in any suitable location within the housing. Furthermore, various electronics and/or other components may be disposed outside of the internal volume of the member 110. For example, one or more proximity sensors (e.g., optical sensor) may be disposed on an outer surface of the member 110, as further described below with reference to FIGS. 2A-2C. As another example, one or more capacitive sensors may be disposed on an outer surface of the member 110, as further described below with reference to FIGS. 3A-3C.

In some variations, the user interface device may include at least one motor. For example, as shown in FIG. 1C, a motor 180 may be disposed on a first end of the member 110, at least partially disposed within the internal volume of the member 110. Similarly, as shown in FIG. 2A, a motor 280 may be disposed on a first end of a member 210. However, the motor may be located in any suitable location in or around the member 110. The motor 180 may include a rotary motor, a linear motion motor, or other suitable vibrational or other tactile feedback motor. The motor 180 may be controlled to provide haptic feedback to the user in the form of tactile feedback. For example, a controller may actuate the motor 180 in response to a trigger event in order to communicate the occurrence of that event to the user. Different patterns (e.g., duty cycle, pattern of an irregular on-off cycle, speed, etc.) may indicate different events to the user. Examples of events triggering haptic feedback to the user include actuation of an end effector (e.g., firing of a cauterization tool), loss of communication with the user interface device (e.g., due to power loss, movement of the user interface device outside a trackable workspace, etc.), misalignment of the user interface device relative to a calibrated or known reference frame, detection of potential collision between components of the robotic system (e.g., between robotic arms), etc.

Furthermore, other feedback cues such as audio (tones, warnings, etc. emitted from the user interface device or other aspects of a user console) and/or visual (e.g., light emitted from the user interface device via LEDs or other display) may additionally or alternatively be used to communicate information about particular events to the user. For example, the user interface device may include one or more LEDs (e.g., RGB, white, other suitable colors, etc.) that illuminate alone or in combination in different timing or spatial patterns to indicate different error codes or other information.

In some variations, a separate member 110 may be omitted from the user interface device. In these variations, the tracking sensor system, motor, sensor electronics, etc. described herein as being included in the member 110 may alternatively be contained in a liner member (e.g., liner 1221 as shown in FIG. 12) portion of the housing.

Tracking Sensor System

As shown in FIG. 2A, the user interface device may include a tracking sensor system 240 configured to detect position and/or orientation of the user interface device in free space. For example, the tracking sensor system 240 may include a magnetic tracking probe 242 capable of measuring up to six degrees of freedom, including physical displacement (e.g., in XYZ space or other suitable coordinate system), roll, pitch, and yaw of the user interface device. Suitable magnetic tracking probes or other sensors are known to those of ordinary skill in the art. The tracking probe 242 may be disposed in the member 210 as shown in FIG. 2A, such as within an internal volume of the member 210, or in any suitable location on the member or housing of the user interface device.

The tracking sensor system 240 may additionally or alternatively include other types of sensors for tracking position and/or orientation of the user interface device. For example, the tracking sensor system 240 may include one or more gyroscopes, one or more accelerometers, and/or one or more magnetometers. Some or all such sensors may be part of an inertial measurement unit (IMU). These and other suitable sensors may be disposed on the PCB 260 in the member 210 as shown in FIG. 2A, or in any suitable location on the member or housing of the user interface device. Readings from multiple sensors, such as a magnetic tracking probe 242 and from an IMU, may be used to improve the tracking of position and/or orientation of the user interface device. For example, sensor readings from the tracking probe 242 and the IMU may be used for redundancy purposes, to corroborate each other and/or provide back-up tracking functionality in the event the one or the other experiences failure or is otherwise untrustworthy (e.g., due to signal interference, as described below). As another example, sensor readings from the tracking probe 242 and/or the IMU may be combined (e.g., averaged) to improve overall quality of signal readings from the sensors.

As shown in FIG. 2A, in some variations, the user interface device may include electrical components such as a motor 280 that may cause interference with at least a portion of the tracking sensor system 240 (e.g., the magnetic tracking probe 242) and result in inaccurate determinations of position and/or orientation of the user interface device. In such variations, the user interface device may account for the interference in various manners. For example, the sensor readings from the tracking probe 242 may be disregarded for a predetermined window of time after the motor 280 is actuated, in order to disregard signals potentially adversely affected by interference caused by actuation of the motor 280 and/or any other component. During this window of time, measurements from one or more other sensors unaffected by interference (e.g., from accelerometers, gyroscopes, magnetometers, etc.) may be used instead for tracking position and/or orientation of the user interface device. As another example, a suitable offset and/or factor may be applied to the sensor reading, based on a predetermined model of the interference caused by actuation of the motor 280 or other component, in order to compensate for the signal interference.

Other Sensors

In some variations, the user interface device may include one or more sensors for detecting various kinds of user control inputs and/or other states. For example, one or more sensors may be configured to detect gripping or squeezing of the user interface device, gestures (e.g., swiping), disconnect from the user (e.g., dropping of the user interface device), etc. which may be correlatable to a control of the robotic system, such as a robotic arm, an end effector, navigation of a graphical user interface, etc.

Squeeze Sensors

Proximity Sensor with Flexing Arm

In one variation, as shown in FIGS. 2A-2C, the user interface device 200 may include at least one grip or squeeze sensor in the form of a proximity sensor 270 configured to detect deformation of the housing, where the detected deformation of the housing may be correlatable to a control of the robotic system. As shown in FIG. 2A, the proximity sensor 270 may be used in conjunction with a flexible member or arm 272 that is disposed in the member 210 and configured to flex in response to deformation of the housing 220. The arm 272 may have a first end 272a (e.g., proximal end) and a second end 272b (e.g., distal end). The first end 272a may be fixed to the member 210 such as with mechanical interference, epoxy, or other suitable attachment method. The second end 272b and a block 274 disposed on the second end 272b may be free to move relative to the first end 272a with deflection of the arm 272.

When a user grips or squeezes the housing 220, the increased pressure causes the inner wall 222 of the housing to deform. Upon deformation of the inner wall 222 of the housing, the inner wall 222 displaces the block 274 and causes the arm 272 to deflect. The proximity sensor 270, which may be disposed on the PCB 260 opposite the block 274, may be configured to detect deformation of the housing by measuring the proximity (or change in distance) to the block 272. This deformation of the housing, which is related to the degree of flexion of the arm 272, may be correlatable to operation of an end effector (e.g., opening or closing jaws) or other suitable control of the robotic system (e.g., selection of an element on a graphical user interface).

The relationship between the deformation of the housing and proximity sensor measurement may be calibrated by tuning the deflection of the arm 272 in one or more various manners. For example, deflection of the arm 272 may be tuned by selecting the material type (e.g., steel, aluminum), length, thickness, cross-sectional shape, and/or other features of the arm 272. As another example, tuned springs may be coupled to the arm (e.g., at the proximal end 272a) to resist flexion of the arm. As yet another example, in some variations, as shown in FIGS. 2B and 2C, the inner wall 222 of the housing may include a thinner portion 223 aligned with the block 274 such that the thinner portion 223 deforms more easily (and causes more deflection) in response to a user squeezing the housing. Similarly, the portion 223 of the inner wall 222 may be made thicker such that the thicker portion deforms less easily (and causes less deflection) in response to a user squeezing the housing. As yet another example, the amount of pressure within the bladder or internal volume 226 may be increased or decreased to change the amount of deformation of the housing in response to a user squeezing the housing.

Although only one arm 272 and proximity sensor 272 arrangement is depicted in FIGS. 2A-2C, it should be understood that multiple arms 272 and proximity sensors 272 may be included in the user interface device. For example, two, three, or any suitable number of arm and sensor arrangements may be distributed around the member 210. The arm and sensor arrangements may be equally or unequally distributed circumferentially around the member 210 and/or longitudinally along the member 210 in any suitable pattern. The inclusion of multiple arm and sensor arrangements may, for example, provide more resolution in detecting location of gripping or squeezing (e.g., to distinguish between a squeeze of a proximal end of the housing and a squeeze of a distal end of the housing).

Additionally or alternatively, the proximity sensor 270 may be used to directly measure deformation of the housing 210, such as by detecting proximity (or change in distance) to the inner wall 222 of the housing (or other element coupled to the inner wall 222) in response to the user squeezing the housing.

The proximity sensor 270 may include any suitable type of proximity sensor for detecting proximity or change in distance to the arm 272, block 271, and/or inner wall 222 of the housing. For example, the proximity sensor 270 may include an optical sensor that emits and/or detects returned electromagnetic radiation (e.g., infrared). In other examples, the proximity sensor 270 may include a capacitive sensor, an ultrasonic sensor, a magnetic sensor, an inductive sensor, or other suitable kind of proximity sensor.

Capacitive Sensor

Figure 3A:
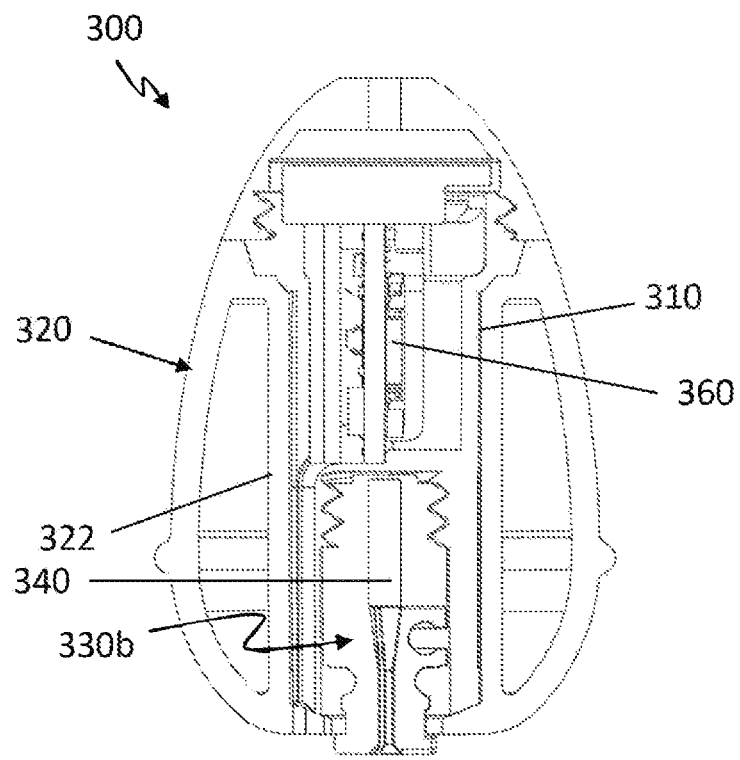
FIG. 3A is a longitudinal cross-sectional view of a variation of a handheld user interface device with a capacitive sensor.
Figure 3B:
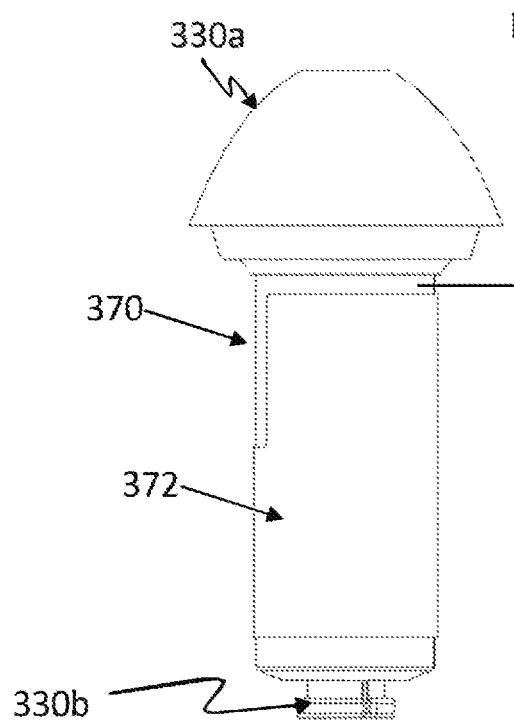
FIG. 3B is an illustrative schematic of a member with a capacitive sensor.
Figure 3C:
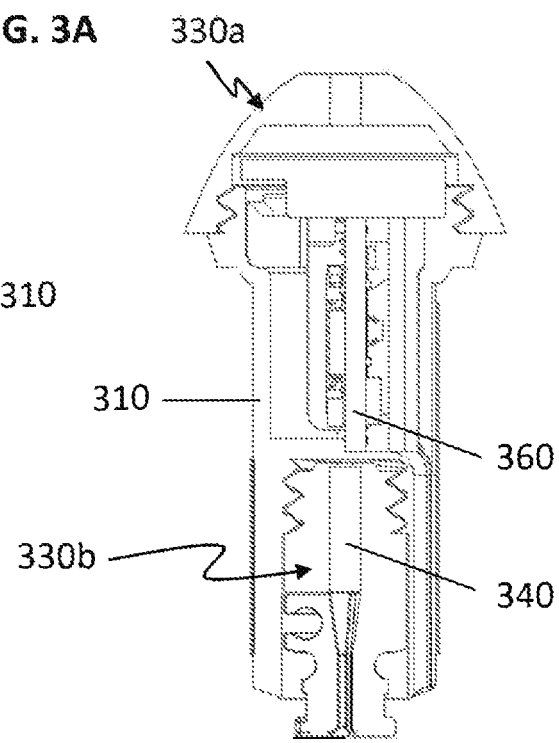
FIG. 3C is a longitudinal cross-sectional view of the member depicted in FIG. 3B.

In some variations, the user interface device may include at least one squeeze sensor including one or more capacitive sensors. For example, in one variation as shown in FIGS. 3A-3C, the user interface device 300 may include at least one squeeze sensor including a capacitive sensor 370 configured to detect interaction between the housing and the hand of the user holding the housing. For example, a capacitive sensor 370 may include a sensor pad 372 disposed on an external surface of the member 310 and configured to detect hand-based squeezing of the housing by measuring proximity (or change in distance) between the hand of the user (as a conductive surface) holding the housing and the member 310. Alternatively, the sensor pad 372 may be disposed on an inner wall 322 of the housing 320, or other suitable fixed reference point in the user interface device.

Figure 4A:
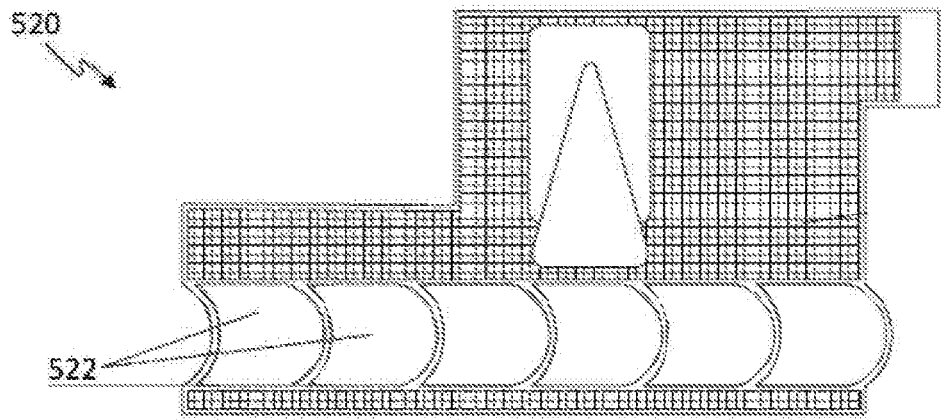
FIGS. 4A and 4B are variations of a capacitive sensor for use in a handheld user interface device.
Figure 4B:
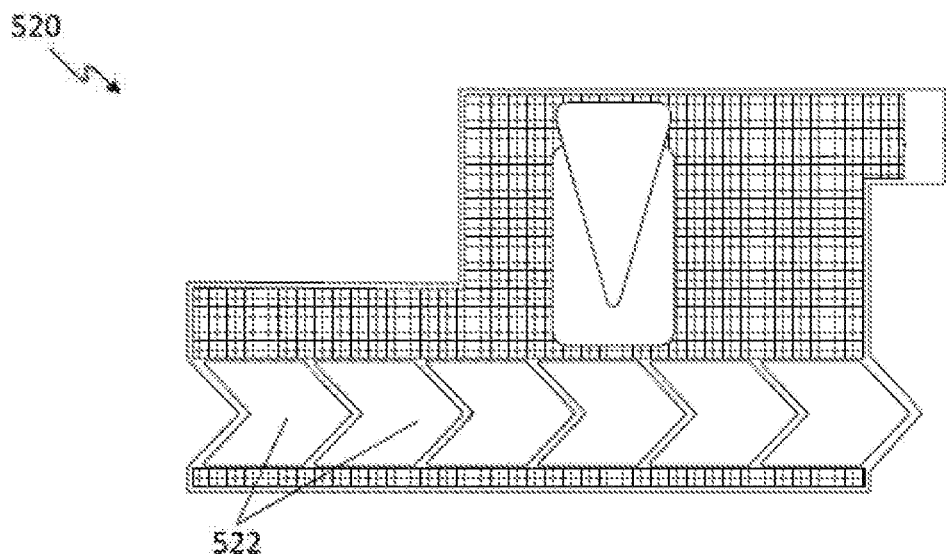
Figure 4C:
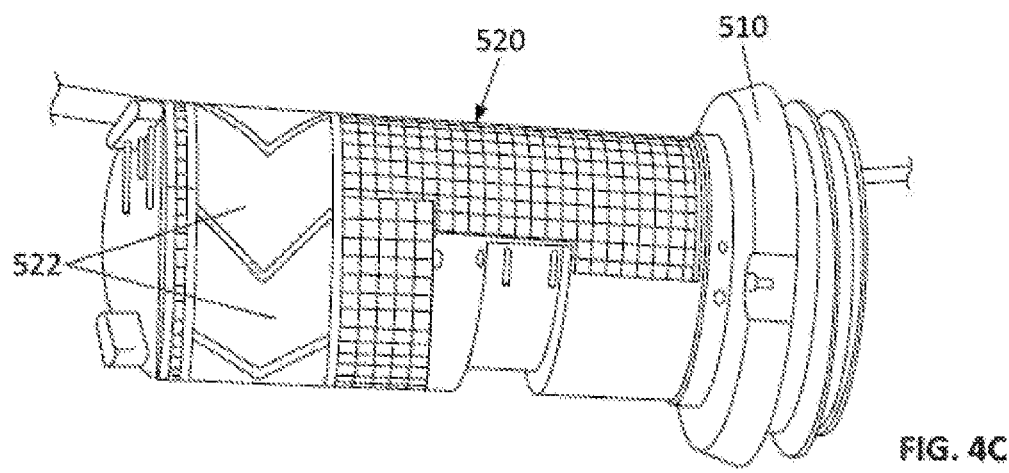
FIG. 4C is an exemplary illustration of a capacitive sensor disposed on a member for use in a handheld user interface device.

As shown in FIG. 3B, the sensor pad 372 may wrap around the external surface of the member 310, and may have a terminal end that passes through a slot in the member 310 to couple to a PCB 360 disposed within the member 310. FIGS. 4A and 4B depict examples of a capacitive sensor pad 520 similar to the sensor pad 372 depicted in FIGS. 3A-3C. The capacitive sensor pad 520 may include, for example, a flex circuit with one or more discrete conductive regions 522. The conductive regions 522 may be arranged along the width of the capacitive sensor pad 520 such that when the capacitive sensor pad 520 is wrapped around the member 510 as shown in FIG. 4C, the conductive regions 522 are arranged circumferentially as a ring around the member 510.

In the examples of capacitive sensor pads 520 depicted in FIGS. 4A and 4B, the capacitive sensor pads 520 may include six discrete regions 522. However, it should be understood that the capacitive sensor pad 520 may include fewer than six regions (e.g., two, three, four, or five) or more than six regions (e.g., seven, eight, nine, ten, etc.). Furthermore, for purposes of detecting squeezing of the housing based on proximity between the capacitive sensor pad 520 and the hand of the user, it may be sufficient for the capacitive sensor pad 520 to include solely one region 522 extending fully or partially circumferentially around the member 510 (e.g., extending to a suitable set of locations underlying where the user is likely to grasp the housing).

The regions 522 may have any suitable shape and arrangement. For example, as shown in FIG. 4A, the shape of the regions 522 may generally approximate the imprint outline or pattern of fingertips. As another example, as shown in FIG. 4B, the shape of the regions 522 may have a chevron pattern. However, some or all of the regions 522 may be rectangular, circular, parallelogrammical, curved, or other suitable shape. Furthermore, although the regions 522 are depicted in FIGS. 4A and 4B as a unilinear array, in other examples the regions 522 may be arranged in any other suitable rectilinear array of any suitable size, or any other suitable pattern or arrangement.

In some variations, the user interface device 300 with a capacitive sensor 370 may incorporate a calibration routine to calibrate the capacitive sensing for a particular user. Different users may have different-sized hands, resulting in different baseline levels of skin surface area contacting the housing. Consequently, different users may need to apply different amounts of force and/or deformation/displacement to generate the same signal level from the capacitive sensor pad 370. Without calibration, different users may need to apply different amounts of force to produce the same effects or control inputs. One example of a calibration routine may include recording the signal level produced when the user squeezes the housing with a predetermined reference amount of force, and using the relationship between the force and the resulting signal level to map signal levels to control inputs (e.g., for actuating the end effector) for that particular user. However, other suitable calibration routines to compensate for differences among individual users may additionally or alternatively be used.

In some variations, the change in capacitance between the capacitive sensor 370 may be compared to multiple predetermined thresholds. For example, when the change in capacitance exceeds a first, lower threshold, this may indicate that the user has squeezed the housing lightly, and this light squeezing action may be correlated to a first user command for the robotic surgical system. As another example, when the change in capacitance exceeds a second, higher threshold, this may indicate that the user has squeezed the housing more heavily, and this heavier squeezing action may be correlated to a second user command for the robotic surgical system.

Timing between measured capacitance changes and/or duration of measured capacitance changes may additionally and/or alternatively be correlated to a sequence of a particular user commands. For example, two (or more) successive detected squeezes may be interpreted similar to a "double click" action for a particular user command. As another example, rhythmic successive detected squeezes (e.g., long, short, long) may be interpreted as another user command.

Figures 14A, 14B:
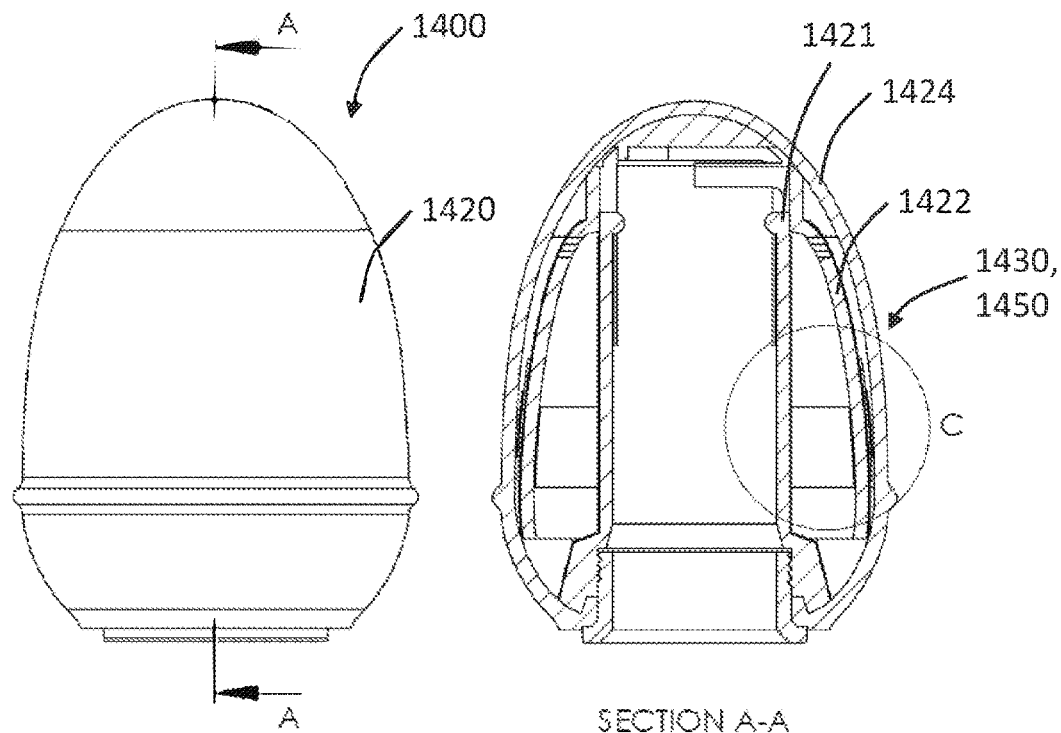
FIGS. 14A and 14B are side and longitudinal cross-sectional views, respectively, of another variation of a handheld user interface device with a capacitive squeeze sensor and a capacitive gesture tracking sensor.
Figure 14C:
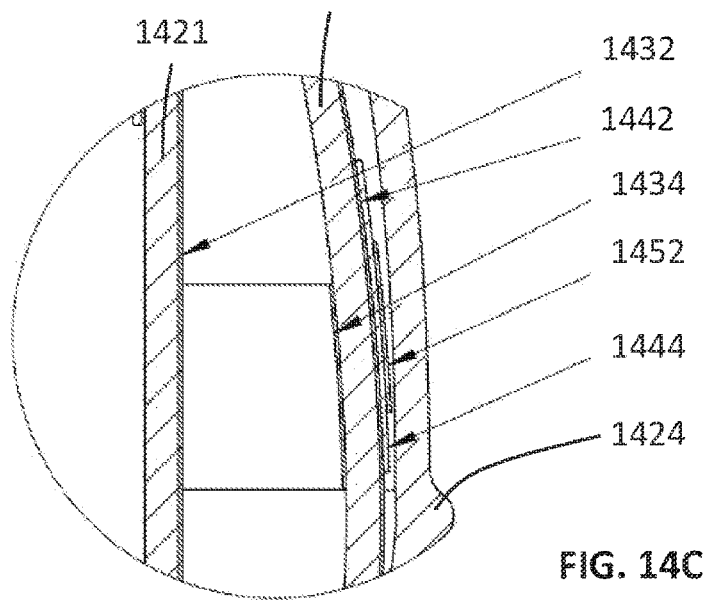
FIG. 14C is a detailed cross-sectional view of the handheld user interface device depicted in FIGS. 14A and 14B.

In another exemplary variation, as shown in FIGS. 14A-14C, a user interface device 1400 may include at least one squeeze sensor including a capacitive sensor 1430 configured to detect interaction between two layered portions of the housing 1420 as the result of a hand of a user interacting with the housing. Similar to the housing 1220 shown in FIG. 12, the housing 1420 may include an inner housing layer 1422 and an outer housing layer 1424. The inner housing layer 1422 may be disposed over a liner 1421 (or alternatively, a member similar to member 110 described above with reference to FIG. 1C) and cooperate with the liner 1421 (or other member) to form a deformable volume between an outer surface of the liner 1421 and the inner surface of the inner housing layer 1422. The capacitive sensor 1430 may include a first conductive surface (or electrode) and a second conductive surface (or electrode) such that the capacitive sensor 1430 may be configured to detect a squeeze of the housing by measuring proximity between the first and second conductive surfaces. For example, as shown in FIG. 14C, the capacitive sensor 1430 may include a first conductive surface 1432 (e.g., electrode) disposed on a surface of the liner 1421 and a second conductive surface 1434 (e.g., electrode) disposed on the inner housing layer 1422 such that the first and second conductive surfaces 1432 and 1434 face each other. The first conductive surface 1432 may be a ground electrode and the second conductive surface 1434 may be an active "gripper" electrode for providing a capacitive signal, or vice versa. Distance between the liner 1421 and the inner housing layer 1422 may be measured based on the capacitance between the first and second conductive surfaces 1432 and 1434. Generally, when the housing 1420 is squeezed (e.g., by the hand of a user holding the user interface device 1400), the inner housing layer 1422 may be compressed toward the liner 1421, thereby moving the first and second conductive surfaces 1432 and 1434 are toward each other. The measured distance between the first and second conductive surfaces 1432 and 1434 may be proportional to the amount of squeezing imparted by the user on the housing 1420. Accordingly, the action of a user squeezing the housing 1420 may result in a change in capacitance measured between the first and second conductive surfaces 1432 and 1434. When the change in capacitance exceeds a predetermined threshold, this change in capacitance may indicate that the user has squeezed the housing, and this action may be correlated to particular user command for the robotic surgical system.

Similar to that described above for the capacitive sensor 370, in some variations, the change in capacitance between the first and second conductive surfaces 1432 and 1434 may be compared to multiple predetermined thresholds. Timing between measured capacitance changes and/or duration of measured capacitance changes may additionally and/or alternatively be correlated to a sequence of particular user commands.

In some variations, the first conductive surface 1432 may include a conductive pad, conductive tape, conductive fabric, or other suitable surface including copper, silver, ceramic, or other suitable conductive material. The first conductive surface 1432 may be wrapped around at least part of the circumference of the liner 1421 (or other member, such as one similar to member 110 described above). The first conductive surface 1432 may, in some variations, include a single conductive region that faces the second conductive surface 1434. The single conductive region may, for example, be located on a region of the member 1410 opposing a portion of the housing 1420 that is ordinarily flexed when a user squeezes the housing 1420 between a thumb and two fingers. For example, a change in capacitance between the single conductive region and the second conductive surface 1434 may be correlated to a squeezing user command. In other variations, the first conductive surface 1432 may include multiple, discrete conductive regions arranged circumferentially around the member 1410 and/or axially along the member 1410. The multiple conductive regions may, for example, provide spatial resolution in capacitance values that may be correlated to different gestures. For example, a change in capacitance measured between a first conductive region of the first conductive surface 1432 (e.g., toward a distal end of the member 1410) and the second conductive surface 1434 (e.g., as a result of the user squeezing the portion of the housing overlying the first conductive region) may be correlated to a first user command. Similarly, a change in capacitance measured between a second conductive region of the first conductive surface 1432 (e.g., toward a proximal end of the member 1410) and the second conductive surface 1434 (e.g., as a result of the user squeezing the portion of housing overlying the second conductive region) may be correlated to a second user command. Furthermore, in some variations, the location of capacitance changes may be analyzed in combination with timing and/or duration of capacitance changes described above, such that different kinds of squeezes of the housing may be correlated to different user commands.

Like the first conductive surface 1432, the second conductive surface 1434 may include a conductive pad, conductive tape, conductive fabric, or other suitable surface including copper, silver, ceramic, or other suitable conductive material. In some variations, the second conductive surface 1434 may be flexible and pliable, such that when the second conductive surface 1434 is coupled to the inner housing layer 1422 as shown in FIG. 14C, the second conductive surface 1434 may move with the inner housing layer 1422 when the housing is squeezed. For example, the second conductive surface may include a conductive silver-coated fabric that is coupled (e.g., via adhesive backing) to the inner housing layer 1422. The second conductive surface 1434 may be disposed along at least part of the inner surface of the inner housing layer 1422 that faces the first conductive surface 1432. Similar to the first conductive surface 1432, the second conductive surface 1434 may include a single conductive region that faces the second conductive surface 1434 (e.g., an inner ring disposed around the inner housing layer 1422). The single conductive region may, for example, be located in a region of the housing 1420 that is ordinarily flexed when a user squeezes the housing 1420 between a thumb and two fingers. For example, a change in capacitance between the single conductive region and the first conductive surface 1434 may be correlated to a squeezing user command. In other variations, the second conductive surface 1434 may include multiple, discrete conductive regions arranged circumferentially around and/or longitudinally along the inner housing layer 1422. The multiple conductive regions may, for example, be conductive regions providing spatial resolution in capacitance values that may be correlated to different gestures, similar to that described above for multiple conductive regions in the first conductive surface 1432.

Gesture Detection Sensors

In some variations, the user interface device may include one or more gesture detection sensors in the form of a capacitive sensor configured to detect interaction between the housing and the hand of the user holding the housing. For example, a capacitive sensor may be used to detect gestures, such as swiping, tapping, tapping-and-holding, double-clicking, etc. Gestures may, for example, be used to navigate a graphical user interface (e.g., navigating through different screens, indicating selection or confirmation of an item, etc.). Additionally or alternatively, gestures may be used as a finger clutch, such as to toggle between control of different aspects of the robotic system (e.g., distinguish between control of a robotic arm and control of an end effector, or distinguish between control of an end effector and a graphical user interface, etc.).

For example, as shown in FIGS. 3A-3C, the capacitive sensor 370, which is described above with respect to detecting squeezing of the housing, may additionally or alternatively be used to detect gestures. As such, as described above with reference to FIGS. 4A and 4B, a capacitive sensor 520 with one or more discrete conductive regions 522 may be configured to provide capacitive sensing with spatial resolution, in order to enable detection of gestures across different areas. For example, as shown in the exemplary illustrative grip depicted in FIG. 5, the housing may include at least one gesture touch region 422 (indicated by dashed boundary lines) under which lies the conductive regions 522. In this example, the index finger of the user may touch and gesture over the surface of gesture touch region 422, and the conductive regions 522 on the member beneath the gesture touch region 422 may detect the contact by the user's index finger. Algorithms may interpret the signals from the conductive regions 522 (e.g., based on number of contacts, location of contacts, timing of contacts, etc.) as different gestures. A tap-and-hold gesture may, in some variations, be interpreted as a finger clutch mechanism. Additionally or alternatively, other portions of the capacitive sensor 520 may include discrete conductive regions to provide other gesture-detecting regions.

Figure 14D:
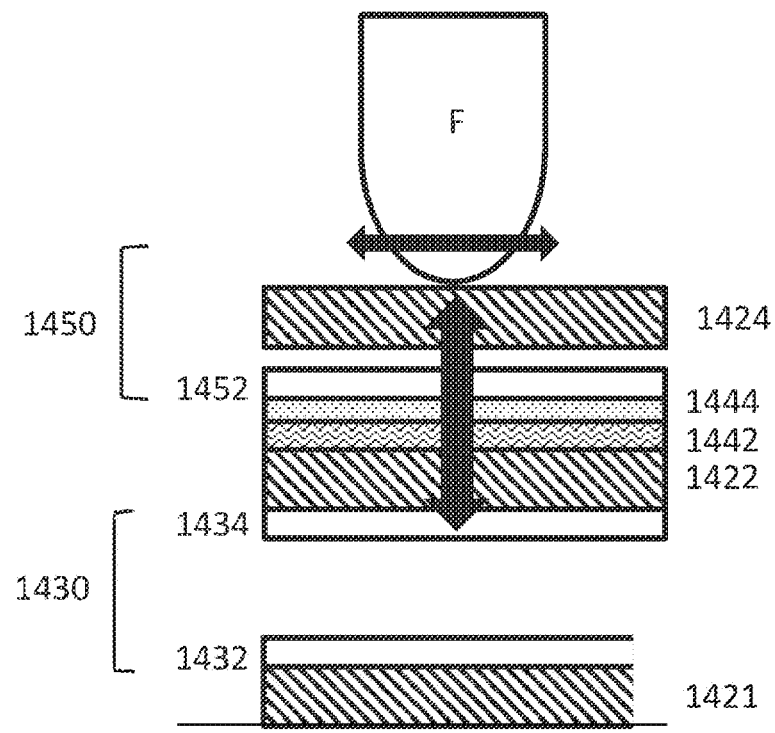
FIG. 14D is an illustrative schematic of layers in the handheld user interface device depicted in FIGS. 14A and 14B.

In some variations, as shown in FIGS. 14C and 14D, a user interface device may include separate capacitive sensors for detecting squeezing (e.g., similar to capacitive sensor 1430 described above) and for detecting gestures. For example, in addition to the first and second conductive surfaces 1432 and 1434 (e.g., ground electrode and gripper electrode) described above for detecting squeezing of the housing, the user interface device may further include a third conductive surface 1452 (e.g., "touch" electrode) in a gesture tracking sensor 1450 configured to detect gestures made by the user on the surface of the housing 1420.

FIG. 14D is a detailed schematic of a portion of an exemplary housing including both a capacitive squeeze sensor 1430 and a capacitive gesture tracking sensor 1450. The squeeze sensor 1430 may include a first conductive surface 1432 (e.g., ground electrode) coupled to the liner 1421, and a second conductive surface 1434 (e.g., gripper electrode) coupled to the inner surface of the inner housing layer 1422, as described above. When a user's hand squeezes the housing as represented by the vertical arrow, the user's finger F may compress the inner housing layer 1422 (and other parts of the housing) toward the liner 1421, thereby changing the distance between the first and second conductive surfaces 1432 and 1434, as described above. Additionally, the capacitive gesture tracking sensor 1450 may include a third conductive surface 1452 disposed between the inner housing layer 1422 and the outer housing layer 1424. The third conductive surface 1452 (e.g., touch electrode) may include one or more discrete conductive regions similar to the capacitive sensor 370 described above, for detecting capacitance based on number, location, timing, etc. of contacts by the user's hand with the housing. When a user's hand performs gestures as represented by the horizontal arrow, the user's finger F may travel across the surface of the outer housing layer 1424 and cause changes in capacitance measured by one or more of the discrete conductive regions on the third conductive surface 1452. Accordingly, such changes may be interpreted and correlated to one or more various user commands, as described above.

The housing may further include at least one shield layer 1442 disposed on the outer surface of the inner housing layer 1422. The shield layer may protect the conductive surface 1452 of the gesture tracking sensor 1450 against electromagnetic interference from conductive surfaces 1432 and 1434 of the squeeze sensor 1430. The shield layer 1442 may be disposed between the second conductive surface 1434 and the third conductive surface 1452 (e.g., coupled to the inner housing layer 1422). Additionally or alternatively, the housing may further include at least one insulating layer 1444 for protecting the conductive surface 1452 of the gesture tracking sensor 1450 against conductive or electrical signals from the conductive surfaces 1432 and 1434 of the squeeze sensor 1430. The insulating layer 1444 may be disposed between the second conductive surface 1434 and the third conductive surface 1452 (e.g., coupled to the shield layer 1442). The insulating layer 1444 may include, for example, foam, plastic, or any suitable material with low conductivity. In some variations, the housing may include insulating and shielding materials combined in one composite layer. Furthermore, although the shield and insulating layers are shown in a particular order between the second conductive surface 1434 and the third conductive surface 1452, it should be understood that their layered arrangement may be the reverse of what is shown in FIG. 14D.

Alternatively, the user interface device may omit the capacitive squeeze sensor 1430 (e.g., and include another suitable squeeze sensor such as those described herein, or omit a squeeze sensor) but still include a conductive surface 1452 as a touch electrode for detecting gestures.

Temperature Sensors

Figure 5:
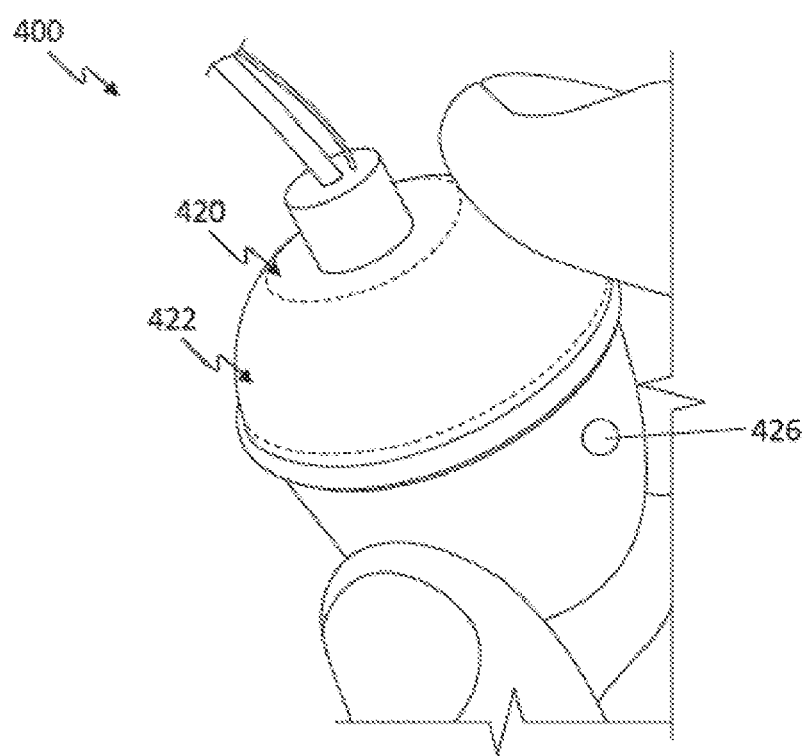
FIG. 5 is an illustration of a variation of a handheld user interface device with a capacitive sensor and a gesture tracking region, held in a hand of a user.

In some variations, the user interface device may include one or more temperature sensors. In one variation, one or more temperature sensors may be configured to detect temperature of the user. For example, as shown in FIG. 5, a temperature sensor 426 may be located on an external surface of the housing 420 and be configured to measure temperature of the user based on contact with the user's fingers. The temperature of the user may be used as an indicator of stress level for the user. If the user's temperature rises beyond a threshold level, the user interface device 400 may indicate this danger to the user through a warning system (e.g., through a controller), and may prompt the user to suspend operation of the robotic system. Additionally or alternatively, the temperature of the user may be used to provide data for a calibration routine similar to that described above for the capacitive sensor 370, as different users having different temperatures may need to apply different amounts of force to generate the same signal level from the capacitive sensor pad 372.

In another variation, one or more temperature sensors may be configured to detect temperature within the user interface device and/or ambient temperature. For example, a temperature sensor may be disposed on a PCB (e.g., PCB 260 shown in FIGS. 2A and 2B, PCB 360 shown in FIGS. 3A-3C, etc.) within the member. The temperature within the user interface device and/or ambient temperature may be used to correct or compensate for drift in capacitive and other sensor measurements, as part of a calibration routine at the outset of a procedure and/or dynamically throughout the procedure.

Drop Sensors

In some variations, the user interface device may include one or more drop detection sensors configured to determine when the user's hands have disconnected from the user interface device, in order to trigger suspension of communications between the user interface device and control of the robotic system, thereby avoiding inadvertent or unintentional commands to the robotic system.

In one variation, the drop detection sensors may include a capacitive sensor similar to the capacitive sensor 370 described above with reference to FIGS. 3A-3C and/or either of the capacitive sensors 1430 and 1450 described with reference to FIGS. 14A-14D. Such a capacitive sensor (e.g., for detecting a squeeze of a housing and/or gestures on the housing) may additionally or alternatively be used to detect when the user is no longer holding the user interface device. For example, the capacitive regions 522 may be used to detect when the user's fingers are no longer proximate the housing due to a sudden drop of capacitance below a predetermined threshold.

In another variation, the drop detection sensors may include at least one accelerometer and/or at least one gyroscope, which may be individual sensors or incorporated as part of an IMU. The accelerometer and/or gyroscope may be configured to detect a sudden downward drop due to gravity when the user is no longer holding the user interface device and the user interface device is thereafter allowed to fall downward.

In another variation, the tracking sensor system of the user interface device (e.g., tracking sensor system 140 shown in FIG. 1C, tracking sensor system 240 shown in FIG. 2A, tracking sensor system 340 shown in FIG. 3A, etc.) may be used as a drop detection sensor. For example, like the accelerometer and/or gyroscope, the tracking sensor system 140 may detect a sudden downward drop due to gravity when the user is no longer holding the user interface device. Similarly, in other variations, any other suitable tracking sensors (e.g., optical tracking, including optical markers such those attached to an adapter) may be used to detect the downward drop resulting from the user dropping the user interface device.

Any one or more of the above-described drop detection sensors may be used alone or in combination in any suitable manner. For example, multiple drop detection sensors (e.g., capacitive sensor, IMU, and tracking sensor system in combination) may be used to provide redundancy to help confirm whether the user has dropped the user interface device.

Adapters

Figure 6A:
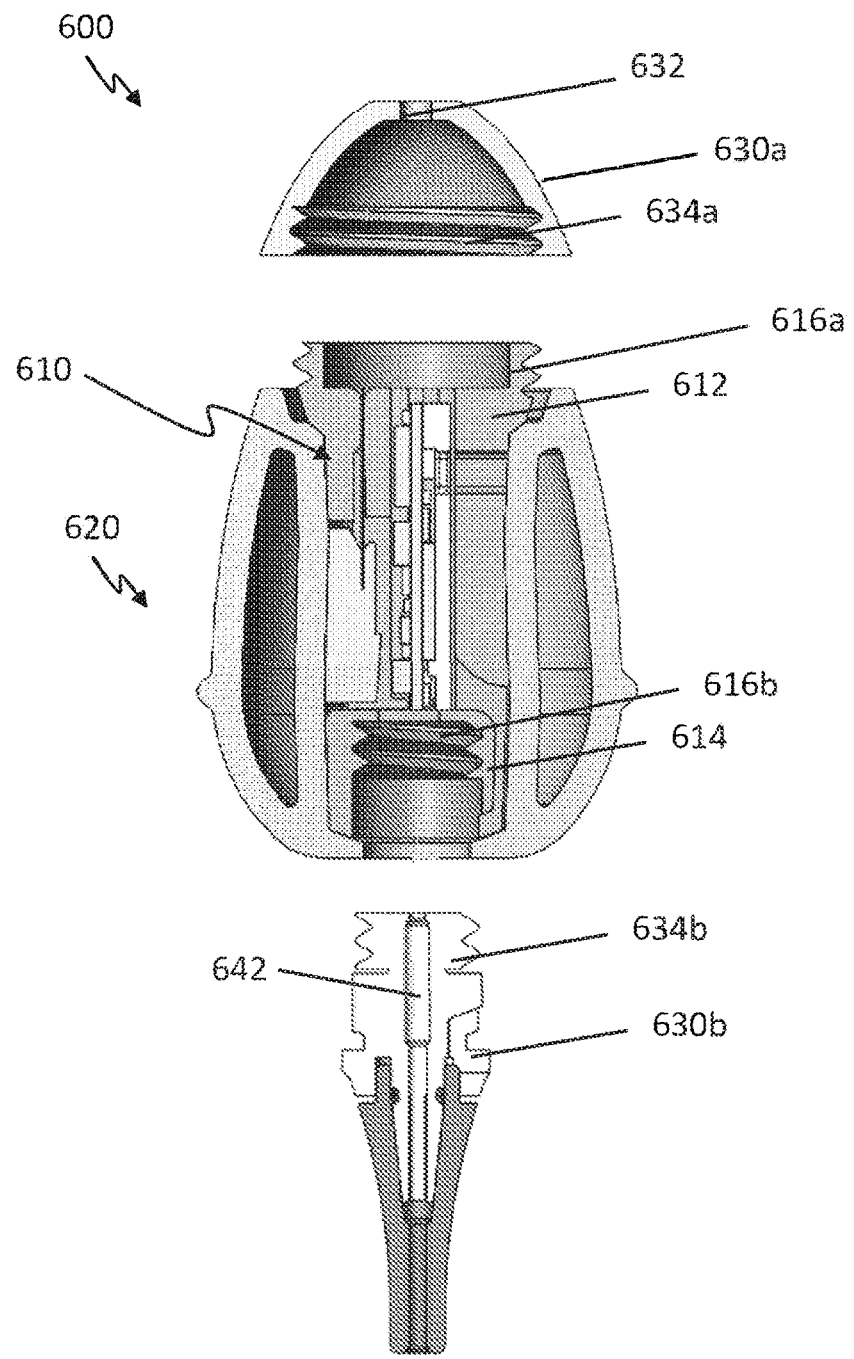
FIG. 6A is a longitudinal cross-sectional view of one variation of a handheld user interface device with modular, interchangeable adapters.

Generally, in some variations, as shown in FIG. 6A, a handheld user interface device 600 for controlling a robotic system may include a member 610 having a first end 612 (e.g., proximal end) and a second end 614 (e.g., distal end), where the first end and/or the second end includes an engagement feature configured to couple to a detachable adapter. Similar to the variations described above, the user interface device 600 may include a housing 620 at least partially disposed around the member 610 and configured to be held in the hand of a user, and a tracking sensor system including a tracking probe 642 and/or other sensors for detecting position and/or orientation of at least a portion of the device. The detachable adapter may be interchangeable with other kinds of detachable adapters, thereby facilitating a modular design permitting multiple configurations of user interface devices such as with different form factors, different functional features, and/or different tracking technologies in various combinations. Examples of detachable adapters are described below with respect to FIGS. 6A-6C, 7A-7C, 8A-8DD, 9A-9C, and 11A-11B.

As shown in FIG. 6A, the engagement feature on the member 610 may include threads that are configured to couple to a threaded interface on a detachable adapter. More specifically, the first end 612 of the member 610 may include a first engagement feature (e.g., proximal engagement feature) and the second end 614 of the member 610 may include a second engagement feature (e.g., distal engagement feature). The first engagement feature may include threads 616a configured to engage threads 634a of a first adapter 630a (e.g., proximal adapter), thereby removably coupling the adapter 630a to the member 610. Similarly, the second engagement feature may include threads 616b configured to engage threads 634b of a second adapter 630b (e.g., distal adapter). Furthermore, coupling the first adapter 630a and second adapter 630b to the member 610 may adjoin the first adapter 630a and second adapter 630b to the housing 620 to maintain a smooth surface for safe and comfortable handling by the user. Alternatively, in other variations, the adapter 630 may couple directly to the housing 620 via threads or other suitable interface. Similarly, the member 210 depicted in FIG. 2A may include a first engagement feature 216a for coupling a first adapter 230a to the member 210, and a second engagement feature 216b for coupling a second adapter 230b to the member 210. Also similarly, the member 310 depicted in FIGS. 3B and 3C may include a first engagement feature for coupling a first adapter 330a to the member 310 and a second engagement feature for coupling a second adapter 330b to the member 310. Although the engagement features depicted in the figures include threads, other examples of engagement features on the member 610 include snap-on or snap-fit features (e.g., ridges, lips, tabs, etc.), hinges, breakable adhesives (e.g., with low bonding force), elastomeric interfaces (e.g., O-rings, wraparound elastic bands), or any other coupling mechanisms suitable for detachably coupling the member and/or housing to an adapter.

For example, as shown in FIG. 6A, one variation of a user interface device 600 may include or be configured to couple to a cap adapter 630a which covers one end of the member 610 and has threads 634a that removably engage threads 616a on the member 610. The cap adapter 630a may be shaped to promote an overall ovoid shape or other rounded body shape of the user interface device 600. The cap adapter 630a may have at least one hole 632 or other passageway that permits one or more wires to pass in or out of the user interface device, though in other variations (e.g., in a wireless user interface device) the hole 632 may be omitted. Furthermore, FIG. 6A depicts another variation of an adapter, a probe housing 630b for a tracking probe 642. The probe housing 630b may include threads 634b that removably engage threads 616b on the member 610. The probe housing 630b may be configured to protect the tracking probe 642 and provide a vehicle for inserting and securing the tracking probe 642 into the member 610.

Figure 6B:
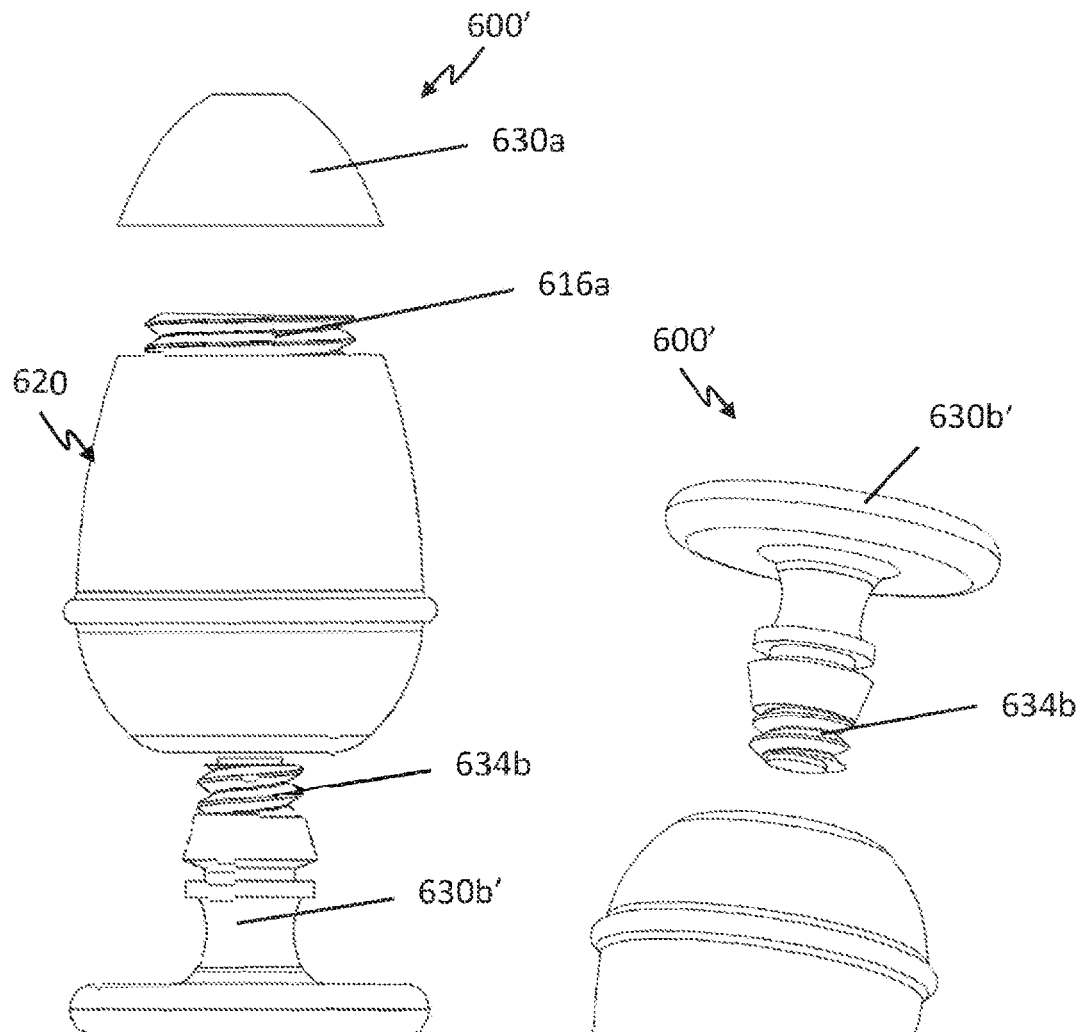
FIGS. 6B and 6C are side and perspective views of another variation of a handheld user interface device with modular, interchangeable adapters.
Figure 6C:
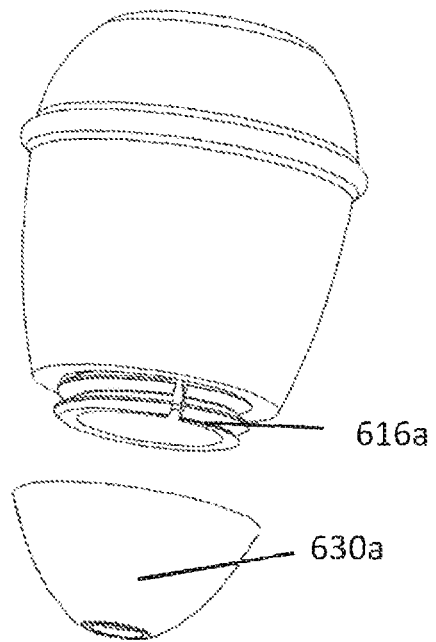

As another example, as shown in FIGS. 6B and 6C, another variation of a user interface device 600' may include or be configured to couple to a cap adapter 630a which covers one end of the member (not shown) and has threads that removable engage threads 616a, similar to the variation shown in FIG. 6A. Furthermore, FIGS. 6B and 6C depict another variation of an adapter, a disc adapter 630b' which may include threads 634b that removable engage corresponding threads on the member. The disc adapter 630b' may be similar, for example, to that described below with respect to FIGS. 9A and 9B.

As shown in FIGS. 7A-7B, one variation of a user interface device 700 may include or may be configured to couple to an optical tracking adapter 730 which may removably couple to the member to form a user interface device 700 whose position and/or orientation is trackable with cameras monitoring the optical tracking adapter 730. The optical tracking adapter 730 may include one or more optical tracking markers 732 disposed on at least one face of the optical tracking adapter 730. In one example, the optical tracking markers 732 are passive and include a retroreflective material such that position and/or orientation of the user interface device may be detected with strategically-placed cameras monitoring the optical tracking adapter 730. The cameras may illuminate the workspace of the user interface device 700 with infrared (IR) light (or other suitable emission), and the optical tracking markers 732 may reflect the IR light back to the cameras. As another example, the optical tracking markers 732 may be active (e.g., include light-emitting diodes) that emit IR light (or other suitable emission) toward strategically-placed cameras. Based on this reflection or emission of light from the optical tracking markers 732, the optical tracking system may determine the three-dimensional position and/or orientation of the user interface device 700. For example, as shown in FIG. 7C, a user may hold the housing 720 of the user interface device 700 in such a manner that the optical tracking adapter 730 faces outward and may be in the line of sight of surrounding cameras. Optical tracking markers may be spherical to increase the range of angles of light that the optical tracking markers may reflect or emit, though other types of optical trackers (e.g., flat markers) may additionally or alternatively be used.

As shown in FIG. 7B, one variation of the optical tracking adapter 730 is generally in the shape of a truncated triangular pyramid that flares outward from the housing 720. However, the optical tracking adapter 730 may be square pyramidal, spherical, prismatic, or any other suitable shape for providing surfaces for optical tracking markers 732 to reflect or emit light toward cameras.

Figure 8A:
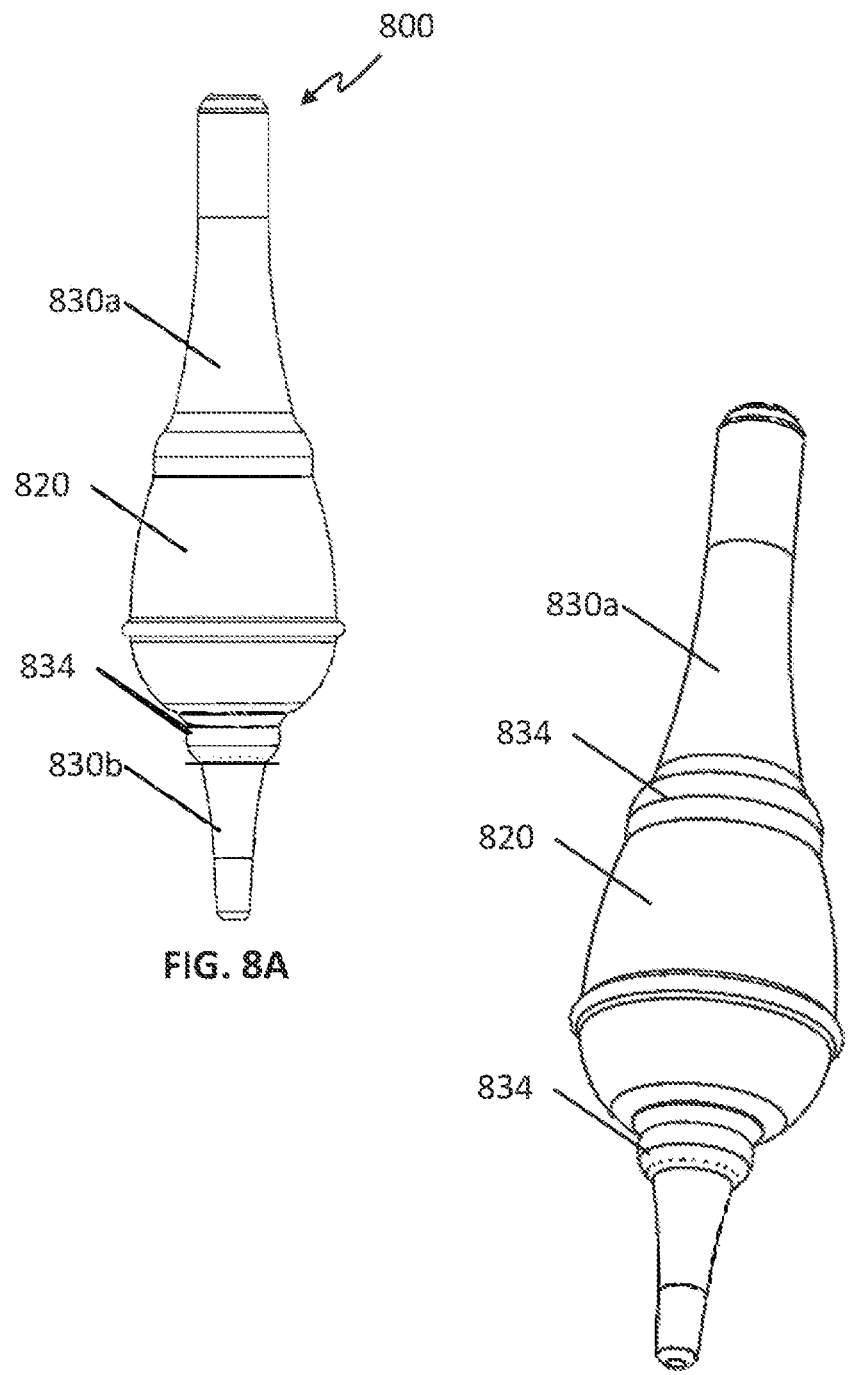
FIGS. 8A and 8AA are side and perspective views of one variation of a handheld user interface device with a stylus adapter.
Figure 8B:
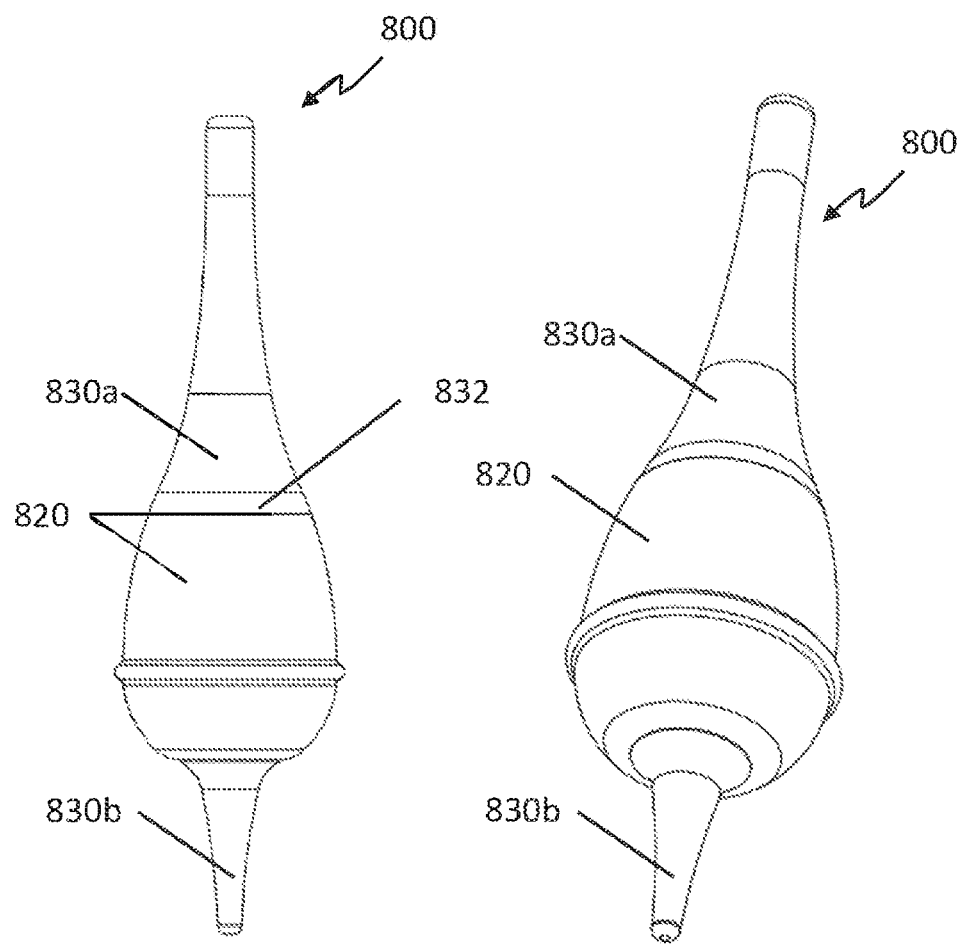
FIGS. 8B and 8BB are side and perspective views of another variation of a handheld user interface device with a stylus adapter.
Figure 8C:
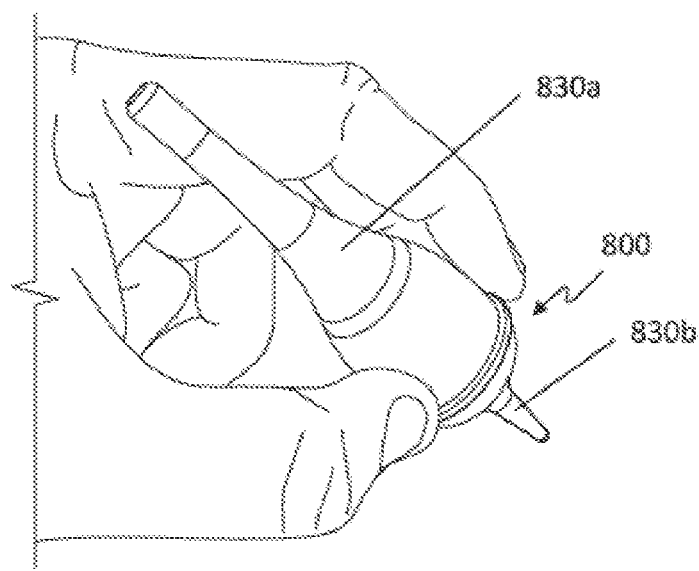
FIG. 8C is an exemplary illustration of the handheld user interface device depicted in FIG. 8B.

As shown in FIGS. 8A, 8AA, 8B, 8BB, 8D, and 8DD, one variation of a user interface device 800 may include or be configured to couple to a proximal stylus adapter 830a and/or a distal stylus adapter 830b. The proximal stylus adapter 830a may be elongated to provide a resting surface enabling the user interface device 800 to rest on the hand of the user as shown in FIG. 8C. The proximal stylus adapter 830a may taper down to a comfortable girth, and/or may include a circular cross-sectional shape, triangular cross-sectional shape, or other polygonal cross-sectional shape. Different lengths, girths, radii of curvature or taper from the housing 820 toward the end of the stylus adapter 830a, cross-sectional shape, and/or other dimensions may be customized or otherwise available for different user hand sizes or shapes, user preferences, and/or applications. For example, the proximal stylus adapter 830a shown in FIGS. 8B and 8BB is generally narrower and longer than the proximal stylus adapter 830a shown in FIGS. 8A and 8AA. As another example, the proximal stylus adapter 830a shown in FIGS. 8D and 8DD is generally longer than the proximal stylus adapter 830a shown in FIGS. 8B and 8BB. Furthermore, in some variations, as shown in FIGS. 8A and 8AA, the user interface device 800 may include one or more buttons 834 (shown as circumferential rings at one or both ends of the housing, but may alternatively be disposed on an elongated surface of the proximal and/or distal stylus adapter, etc.). Furthermore, such ring buttons or other suitable buttons may be included in any other suitable kind of proximal and/or distal adapters.

Figure 11A:
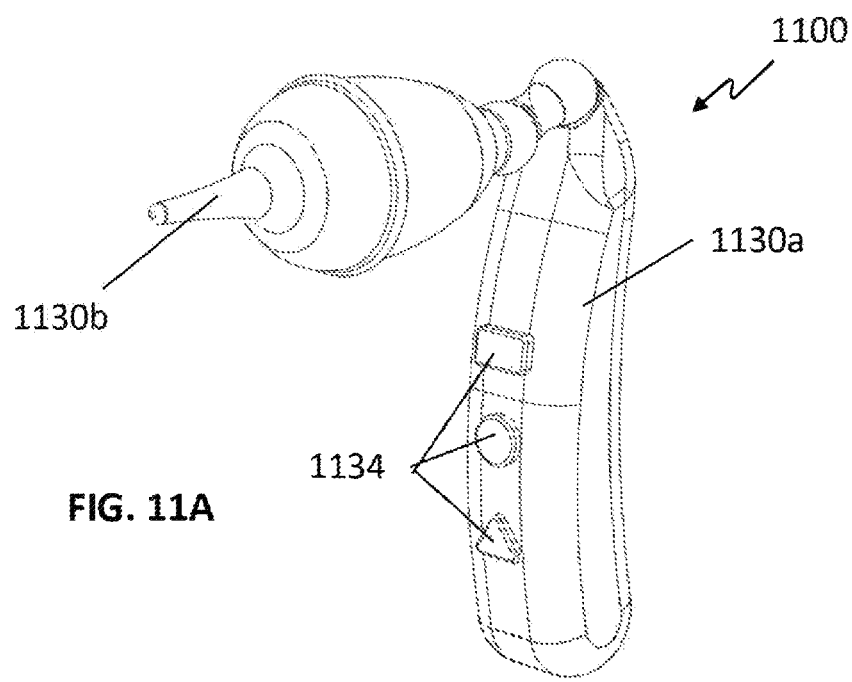
FIGS. 11A and 11B are perspective and side views of another variation of a handheld user interface device with an angled adapter.
Figure 11B:
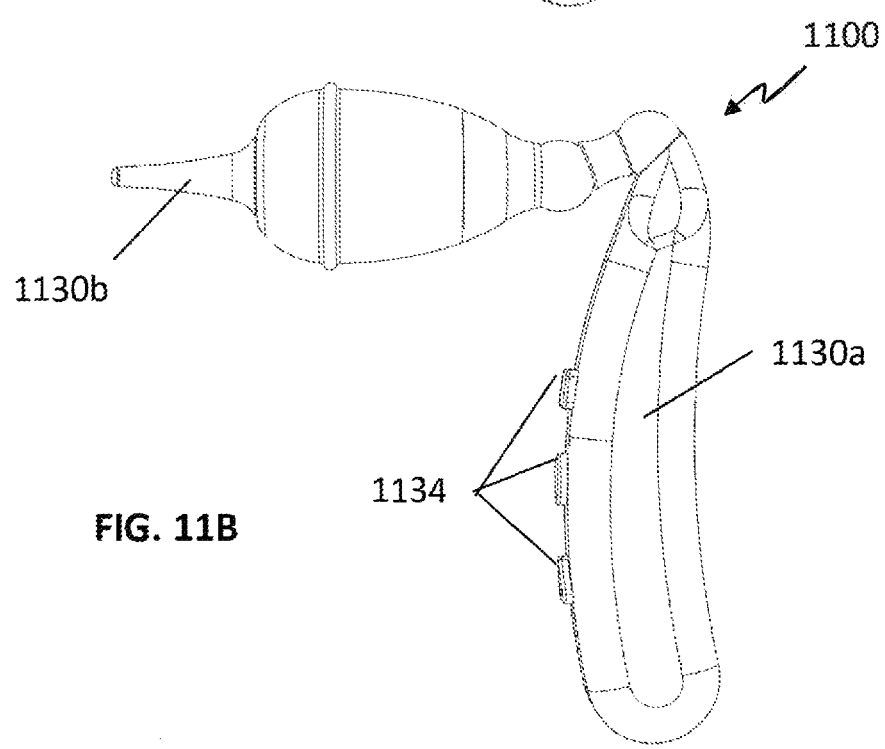

The interface between the proximal stylus adapter 830a and the member (not shown) or housing 820 may be similar to the engagement features described above. In one example, the proximal stylus adapter 830a may be connected via a hinge (or ball joint, etc.) at joint 832 to the member or the housing 820 such that the proximal stylus adapter 830a may be oriented at an angle relative to the longitudinal axis of the housing 820 (e.g., orthogonal, more than 90 degrees, or less than 90 degrees relative to the longitudinal axis of the housing 820). This angled stylus configuration may be useful for providing more ergonomic control of the user interface device in certain applications. As one example, as shown in FIGS. 11A and 11B, one variation of a user interface device 1100 may include or be configured to couple to a proximal stylus adapter 1130a that is angled (e.g., at approximately a right angle) and configured to be held in the palm of a user's hand, and/or a distal stylus adapter 1130b (e.g., which may be similar to distal stylus adapter 830b). At least a portion of the user interface device 1100, such as a surface of the proximal stylus adapter 1130a that is accessible to the user's fingers, may include one or more buttons 1134 configured to further receive user input for controlling an aspect of the robotic system. Such buttons may, for example, have distinguishing shapes (e.g., circle, triangle, square, star, etc.) and/or textures (e.g., dimpled or not dimpled, with bumps or without bumps, etc.) to help enable a user to distinguish between different buttons based on touch, and/or may have different visual indicators (e.g., color) to help enable a user to distinguish between different buttons based on their appearance. Some or all of the buttons may additionally or alternatively include touch sensors or other suitable sensors that may enable, for example, audio feedback (e.g., tones or beeps, etc.) to help enable a user to distinguish between different buttons based on sounds when certain buttons are touched or otherwise engaged.

The distal stylus adapter 830b may be elongated and taper to a finer point. The distal stylus adapter 830b may, for example, be used to modify the user interface device 800 for precision work applications (e.g., cauterization) where a pen-like grip on the user interface device may provide additional precision or comfort to the user. The distal stylus adapter 830b may include a generally circular cross-sectional shape, triangular cross-sectional shape, or other polygonal cross-sectional shape. The distal stylus adapter 830b may be shorter than the proximal stylus adapter 830a, but like the proximal stylus adapter 830a, the distal stylus adapter 830b may vary in length, girth, radii of curvature or taper, cross-sectional shape, and/or other dimensions for different user hand sizes or shapes, user preferences, and/or applications.

The proximal stylus adapter 830a and/or the distal stylus adapter 830b may include a rigid material or semi-rigid material (e.g., rigid plastic). In some variations, the proximal stylus adapter 830*a* and/or the distal stylus adapter 830*b* may include a flexible or compliant material (e.g., silicone).

Figures 9A, 9B:
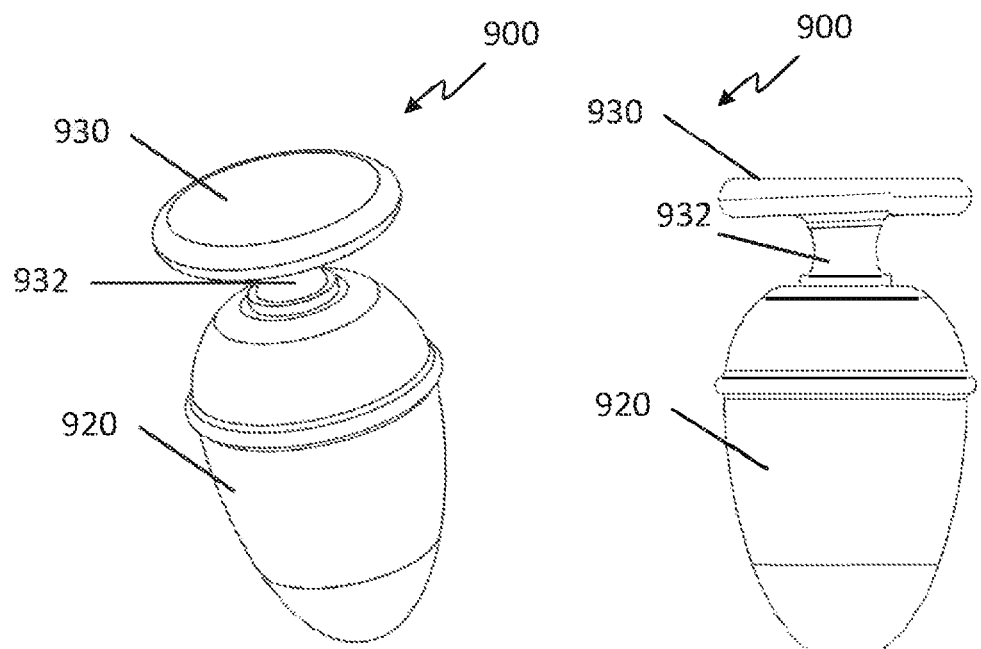
FIGS. 9A and 9B are perspective and side views of one variation of a handheld user interface device with a disc adapter.
Figure 9C:
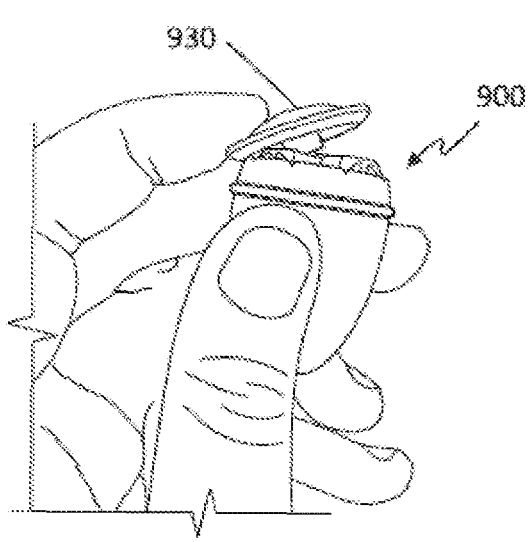
FIG. 9C is an exemplary illustration of the handheld user interface device depicted in FIGS. 9A and 9B.

As shown in FIGS. 9A and 9B, one variation of a user interface device 900 may include or be configured to couple to a disc adapter 930. As shown in FIG. 9C, disc adapter 930 may be configured to tilt, similar to a joystick. The disc adapter 930 may additionally or alternatively be configured to be laterally displaced to the side (i.e., in-plane) and/or axially displaced up or down, similar to a button. In yet other variations, the disc adapter 930 may be configured to rotate axially, similar to a steering wheel. The disc adapter may, for example, indicate directional-related control inputs (e.g., camera view panning), may be used as a finger clutch to toggle between control modes, and/or may be used as a button to indicate actuation of an end effector (e.g., firing a tool) or selection of a graphical user interface item, etc.

The shape and/or size of the disc adapter 930 may vary for different kinds (e.g., size, shape, etc.) of users' hands, user preferences, and/or applications. For example, as shown in FIG. 9B, the disc adapter 930 may include a solid, flat circular disc attached with a stem 932 to the member and/or housing 920. However, it should be understood that the disc adapter 930 may alternatively include a noncircular disc (e.g., elliptical or polygonal), a ring, a more bulbous disc, or other suitably-shaped attachment. Furthermore, the length of the stem 932 and/or diameter or thickness of the disc may vary for different users.

Another variation of a user interface device may include or be configured to couple to a pincher adapter. For example, the pincher adapter may include a first pivotable member configured to interface with a first finger of the user (e.g., a thumb) and a second pivotable member configured to interface with a second finger of the user (e.g., an index finger) such that the first and second fingers may grasp and cause the first and second pivotable members to pinch together. The pinching adapter may, for example, be used to provide a mechanical-based control of actuation of jaws or other end effector with opposable motions. The first member and/or second member may include textural features (e.g., ribbings, patterned raised dots) and/or frictional materials (e.g., silicone or other rubber) to reduce slippage of engagement between the user's fingers and the first member and/or second member. Furthermore, the members may be contoured to receive the user's fingers. Straps, rings, hooks, and/or other suitable attachments may be used to securely couple the user's fingers to the pincher members. Furthermore, the length, width, contour, shape and size, and/or other dimensions of the members and/or attachments may vary for different users.

Sterility and Disposability

In some applications, such as for surgical or other medical applications, it may be important to maintain sterility of the user interface device. In some variations, a handheld user interface device may include a member, a housing at least partially disposed around the member, and a tracking sensor system as described above, where at least a portion of the tracking sensor system is removable from the member to enable disposal of at least one of the member and the housing. In some variations, the member (and its associated sensors and other electronics) and/or the housing may be made of inexpensive materials that make it more economically practical or convenient to dispose of after each use instead of resterilizing. In another variation, the member and tracking sensor system may be removable from the housing to enable disposal of at least a portion of the housing.

Figure 14E:
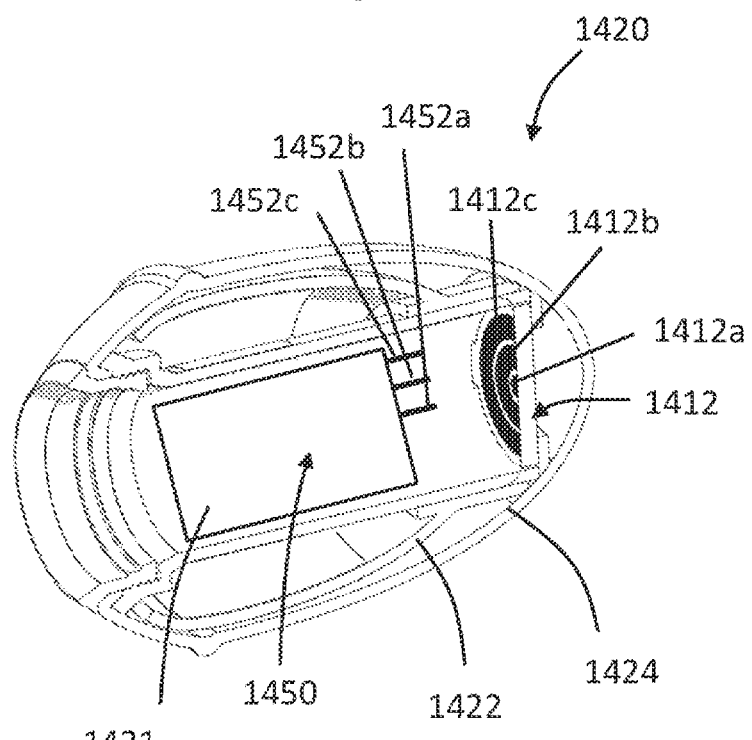
FIG. 14E is a longitudinal cross-sectional view of a handheld user interface device with an electrical contact board disposed in the housing.

As shown in FIG. 14E, in some variations in which the member and tracking sensor system are removable from the housing, it may be desirable to facilitate a secure and easily reversible connection between the member/tracking sensor system and the housing. For example, communication of electronic signals to and from electronics on the housing (e.g., to and from capacitive squeeze and/or gesture tracking sensors as described above with reference to FIGS. 14A-14D) may be accomplished via a "bulls-eye" or ringed conductive contact board 1412. The contact board 1412 may be arranged, for example, in a slot at an end of a liner 1421 disposed within the inner housing layer 1422. The conductive contact board 1412 may include concentric rings of conductive regions for connecting electrical contacts from the member to electrical contacts from the housing. For example, as shown in FIG. 14D, the member 1450 may include one or more conductive (e.g., gold) pins 1452*a*-1452*c* that spaced apart from each other at varying radial distances corresponding to the concentric conductive rings on the contact board 1412. Thus, alignment and positioning of the member 1450 within the liner 1421 automatically accomplishes the desired electrical contact between the pins 1452*a*-1452*c* and respective conductive regions on the contact board 1412. For example, pin 1452*a* may be arranged generally at the center of the member 1450, pin 1452*b* may be arranged at a moderate radial distance away from the center of the member 1450, and pin 1452*c* may be arranged at a far radial distance away from the center of the member 1450.

In some variations, the pins 1452*a*-1452*c* may include at least one "ground" pin coupled to a common electrical ground, and one or more "signal" pins for coupling to one or more sensors. For example, in the capacitive sensor 1430 described above, the first conductive surface 1432 disposed on the liner 1421 may be a ground surface that is conductively coupled to the ground pin via the contact board 1412. Additionally, the second conductive surface 1434 disposed on the inner housing layer 1422 may be an active surface that is conductively coupled to a signal pin via the contact board 1412 for providing capacitance measurements. It should be understood that any other sensors at least partially disposed in the housing 1420 may additionally or alternatively be communicatively coupled to the member 1450 via the contact board 1412.

When the member 1450 is inserted into the liner 1421, the pins 1452*a*, 1452*b*, and 1452*c* may be of suitable length such that their distal ends contact the central region 1412*a*, the middle ring 1412*b*, and the outer ring 1412*c*, respectively. This contact thereby facilitates electrical communication with the capacitive sensor 1430 and/or other housing sensors via the contact board 1412. Secure electrical connection may be accomplished simply by securing the member to the housing. For example, in this variation, there is no need for separate connector adapters or latches dedicated to secure the connection between the pins and the contact board. Of similar simplicity, disconnection of the pins 1452*a*-1452*c* from the contact board 1412 is accomplished simply by removing the member from the housing. Accordingly, this electrical connection arrangement may enable easier partial assembly and disassembly of the member (and/or tracking sensor system) and the housing, such as for easier and more straightforward sterilizing or disposal of the housing. However, any suitable connection scheme may facilitate communication of electronics on the housing and member, such as wires, ribbon cables, conductive traces, etc.

Furthermore, any adapters such as an optical tracker adapter, stylus adapter, or disc adapter, may be disposable. One or more of the member, housing, and adapters may be single-use, meaning that it may be separated from the tracking sensor system for disposal after a single use. One or more of the member, housing, and adapters may alternatively be limited use, meaning that it may be separated from the tracking sensor system for disposal after a limited number of uses (e.g., after between 5-10 uses). Alternatively, the entire user interface device, including the tracking sensor system, may be disposable.

Additionally or alternatively, in some variations, the user interface device may be covered with a sterile drape such as a bag or other covering, which may be replaced between uses of the user interface device in order to maintain sterility.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A handheld user interface device for controlling a robotic system, the handheld user interface device comprising:
   a flexible housing having an inner housing wall and an outer housing wall and is at least partially disposed around a lumen, and is configured to be held in a hand of a user; and
   a capacitive sensor that detects the user squeezing the flexible housing by sensing deformation of the inner housing wall, the sensed deformation is an input for controlling the robotic system.

2. The handheld user interface device of claim 1, wherein the capacitive sensor is at least partially disposed on the lumen.

3. The handheld user interface device of claim 1, wherein the capacitive sensor senses deformation of the inner housing wall by measuring proximity between a first conductive surface on the lumen and a second conductive surface on the inner housing wall.

4. The handheld user interface device of claim 1, wherein the capacitive sensor comprises a plurality of discrete sensor regions that detect gestures performed by the hand of the user on the flexible housing.

5. The handheld user interface device of claim 1, wherein the input correlates to control of an end effector of the robotic system.

6. The handheld user interface device of claim 1, wherein the capacitive sensor is a first capacitive sensor, wherein the handheld user interface device further comprises a second capacitive sensor comprising a plurality of discrete sensor regions that detects gestures performed by the hand of the user on the flexible housing.

7. The handheld user interface device of claim 1 further comprising a sensor that is at least partially disposed on or in the lumen for detecting at least one of position and orientation of the handheld user interface device.

8. The handheld user interface device of claim 7, wherein the sensor is configured to be removed from at least one of the lumen and the flexible housing.

9. The handheld user interface device of claim 1, wherein the flexible housing comprises a fluid-filled internal volume between the inner housing wall and the outer housing wall.

10. The handheld user interface device of claim 1, wherein the flexible housing is configured to couple to the lumen.

11. An apparatus comprising:
   a flexible housing having an inner housing wall and an outer housing wall and is at least partially disposed around and is configured to couple to a lumen; and
   a capacitive sensor arranged to detect squeezing of the flexible housing by sensing deformation of the inner housing wall, the sensed deformation is an input for controlling at least a portion of a robotic system.

12. The apparatus of claim 11, wherein the capacitive sensor is at least partially disposed on the lumen.

13. The apparatus of claim 11, wherein the capacitive sensor senses deformation of the inner housing wall by measuring proximity between a first conductive surface on the lumen and a second conductive surface on the inner housing wall.

14. The apparatus of claim 11, wherein the capacitive sensor comprises a plurality of discrete sensor regions that detect gestures performed by a hand of a user on the flexible housing.

15. The apparatus of claim 11, wherein the input correlates to control of an end effector of the robotic system.

16. The apparatus of claim 11, wherein the capacitive sensor is a first capacitive sensor, wherein the apparatus further comprises a second capacitive sensor comprising a plurality of discrete sensor regions that detects gestures performed by a hand of a user on the flexible housing.

17. The apparatus of claim 11 further comprising a sensor that is at least partially disposed on or in the lumen for detecting at least one of position and orientation of the apparatus.

18. The apparatus of claim 17, wherein the sensor is configured to be removed from at least one of the lumen and the flexible housing.

19. The apparatus of claim 11, wherein the flexible housing comprises a fluid-filled internal volume between the inner housing wall and the outer housing wall.

* * * * *